US008642273B2

(12) United States Patent
Taylor et al.

(10) Patent No.: US 8,642,273 B2
(45) Date of Patent: Feb. 4, 2014

(54) LIGAND SENSING FLUORESCENT ACETYLCHOLINESTERASE FOR DETECTION OF ORGANOPHOSPHATE ACTIVITY

(75) Inventors: Palmer Taylor, Del Mar, CA (US); Zoran Radic, San Diego, CA (US); Jianxin Shi, San Diego, CA (US); Aileen Boyd, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 479 days.

(21) Appl. No.: 10/469,731

(22) PCT Filed: Apr. 16, 2003

(86) PCT No.: PCT/US03/11864
§ 371 (c)(1),
(2), (4) Date: Dec. 1, 2004

(87) PCT Pub. No.: WO03/089599
PCT Pub. Date: Oct. 30, 2003

(65) Prior Publication Data
US 2005/0089926 A1      Apr. 28, 2005

Related U.S. Application Data

(60) Provisional application No. 60/373,108, filed on Apr. 16, 2002.

(51) Int. Cl.
*C12N 9/18* (2006.01)
(52) U.S. Cl.
USPC ........... 435/7.1; 435/7.92; 435/197; 435/174; 435/20
(58) Field of Classification Search
None
See application file for complete search history.

(56) References Cited

U.S. PATENT DOCUMENTS

| | | | |
|---|---|---|---|
| 4,273,866 A | 6/1981 | Voss et al. | 435/7 |
| 4,619,897 A | 10/1986 | Hato et al. | |
| 5,192,507 A | 3/1993 | Taylor et al. | |
| H1344 H | 8/1994 | Baldauf et al. | 435/6 |
| 5,354,654 A | 10/1994 | Liger et al. | |
| 5,624,831 A * | 4/1997 | Vu Khue et al. | 435/177 |
| 6,001,625 A | 12/1999 | Broomfield et al. | |
| 6,326,139 B1 | 12/2001 | Soreq et al. | 435/6 |
| 6,406,876 B1 | 6/2002 | Gordon et al. | 435/20 |

FOREIGN PATENT DOCUMENTS

WO    WO 03/089599    10/2003

OTHER PUBLICATIONS

Boyd et al, "Probing the Active Center Gorge of Acetylcholinesterase by Fluorophores Linked to Substituted Cysteines," (J. Biol. Chem.), vol. 275, No. 29, Jul. 21, 2000, pp. 22401-22408.*
Medline Search online, www.ncbi.nlm.nih.gov/sites/entrez, (search: Protein for AChE), Feb. 27, 2008, 11 pages.*
Shi et al. (2001) J. Biol. Chem. 276(45): 42196-204. Jpub date Nov. 9, 2001, Epub date Aug. 21, 2001.*
Amitai et al., "Fluorescent Organophosphates: Novel Probes for Studying Aging-Induced Conformational Changes in Inhibited Acetylcholinesterase and for Localization of Cholinesterase in Nervous Tissue", *Monographs in Neural Sciences*, 7:70-84 (1980).
Johnson et al., "Mechanistically different inhibitors induce distinct conformations in the omega loop, cys 69-cys 96, of mouse acetylcholinesterase", *FASEB Journal*, 16(4):A556 (2002) print. Meeting info.: Annual Meeting of the Professional Research Scientists on Experimental Biology, one page (abstract).
Shi et al., "Reversibly Bound and Covalently Attached Ligands Induce Conformational Changes in the Omega Loop, $Cys^{69}$-$Cys^{96}$, of Mouse Acetylcholinesterase", *The Journal of Biological Chemistry*, 276(45):42196-42204 (2001).
Enyedy et al., "Molecular dynamics study of active-site interactions with tetracoordinate transients in acetylcholinesterase and its mutants", *Biochem. J.*, 353:645-653 (2001).
Berman et al., Proc Natl Acad Sci USA (1971) 68:395-398.
Bourne et al., J Biol Chem (1999) 274:2963-2970.
Bourne et at, Cell (1995) 83:503-512.
Boyd et al., J Biol Chem (2000) 275:22401-22408.
Cygler et al., Protein Sci (1993) 2:366-382.
De Ferrai et al., I Bioi Chem (2001) 246:23282-23287.
De la Hoz et al., Life Sci (1986) 39:195-199.
Devlin et al., Science (1990) 249:404-406.
Eastman et al., J Biol Chem (1995) 270:19694-20399.
Eckstein et al., Nucleic Acids Research (1985) 13:8749-8785.
Ellman et al., Biochem Pharmacol (1961) 7:88-95.
Goldfrank et al., "Insecticides: Organophosphate and Carbamates" Goldfrank's Toxicologic Emergencies, pp. 1346-1360, 2002.
Grochulski et al., J Biol Chern (1993) 268:72843-72847.
Grochulski et al., Protein Sci (1993) 3: 82-91.
Harel et al., Structure (1995) 3:1355-1366.
Harel et al., J Am Chem Soc (1996) 118:2340-2346.
Harel et al., Proc Natl Acad Sci USA (1993) 90:9031-9035.
International Search Report mailed on Dec. 12, 2003 in International Application No. PCT/US2003/011864 filed on Apr. 16, 2003 and published as WO 2003/089599 on: Oct. 30, 2003.
Kryger et al., Acta Crystallogr Sec D Biol Crystallogr (2000) 56:1385-1394.
Lakowicz, I. R. (1999) Principles of Fluorescence Spectroscopy, 2nd Ed., pp. 185-210, Kluwer Academic Publishers and Plenum Publishing Corp., New York.
Levy et al., Biochem Pharmacol (1986) 35:1079-1085.

(Continued)

*Primary Examiner* — Lisa J Hobbs
(74) *Attorney, Agent, or Firm* — Gregory P. Einhorn; Gavrilovich, Dodd & Lindsey LLP

(57) ABSTRACT

Disclosed are methods for the preparation and use of labeled AChE and labeled AChE inhibitory conjugate compositions for detecting accumulation of toxic materials such as organophosphates, insecticides, and other nerve agents. Also disclosed are methods for the use of labeled AChE and labeled AChE inhibitory conjugate compositions in a variety of areas, including the detecting of toxic materials in biological samples, in the area of food and water analysis, in environmental monitoring, and in industrial settings.

15 Claims, 6 Drawing Sheets

(56) References Cited

OTHER PUBLICATIONS

Lew et al., J Biol Chem (1997) 272:1507-1513.
Marchot et al., J Biol Chem (1993) 268:12458-12467.
Marchot et al., Protein Sci (1996) 5:672-679.
Millard et al., Biochemistry (1999) 38:7032-7039.
Nair et al., Biochemistry (1994) 33:8566-8576.
Pendergast et al., I Biol Chern (1983) 258:7541-7544.
Quinn, D. M., Chem Rev (1997) 87:955-979.
Radic et al., Biochemisrty (1993) 32:12074-12084.
Radic et al., J Biol Chem (1995) 270:20391-20399.
Radic et al., J Biol Chem (2001) 276:4622-4633.
Radic et al., J Biol Chem (1997) 272:23265-23277.
Raves et al., Nat Struct Biol (1997) 4:57-63.
Radic et al., J Biol Chem (1994) 296:11233-11239.
Ripoll et al., Proc Natl Acad Sci USA (1993) 90:5128-5132.
Robards K. and Worsfold P. J., Anal Chem Acta (1992) 266:147.
Rosenberry T. L., Adv Enzymol Relat Areas Mol Biol (1975) 43-:103-218.
Schrag et al., J Mol Biol (1993) 230:575-591.
Scott & Smith, Science (1990) 249:386-390.
Shi et al. (J Biol Chem (2001) 276(45):42196-42204.
Soreq et al., Trends Biochem Sci (1992) 17(9):353-8).
Sussman et al., Science (1991) 253:872-879.
Tai et al., Biophys J (2001) 81:715-724.
Tan et al., Biochemistry (1993) 32:401-403.
Tara et al., Biopolymers (1998) 46:465-474.
Taylor et al., Annu Rev Pharmacol Toxicol (1994) 34:281-320.
Taylor et al., Biochemistry (1975) 14:1989-1997.
Taylor et al., in Basic Neurochemistry, 5th ed., 1993, (Siegal et al., eds.), Chapter 11, pp. 231-260, Raven Press, New York, NY.
Taylor et al., Mol Pharmacol (1974) 10:93-107.
Velan et al., FEBS Lett (1996) 395:22-28.
Wilson, I. B. (1960) in The Enzymes (Boyer, P. D., Lardy. H., and Myrback, K. eds.), (1960) vol. 4, 2nd Ed., pp. 501-520, Academic Press, New York.
Wlodek et al., Biopolymers (2000) 53:265-271.
Wong et al., Biochemistry (2000) 39:5750-5757.
Zhou et al., Proc Natl Acad Sci USA (1998) 95:9280-9283.

\* cited by examiner

LIGAND SENSING FLUORESCENT ACETYLCHOLINESTERASE FOR DETECTION OF ORGANOPHOSPHATE ACTIVITY

RELATED APPLICATIONS

This application is a national phase application claiming benefit of priority under 35 U.S.C. §371 to Patent Convention Treaty (PCT) International Application Serial No: PCT/US2003/011864, filed Apr. 16, 2003, which claims benefit of priority to U.S. Provisional Patent Application Ser. No. 60/373,108, filed Apr. 16, 2002. The aforementioned applications are expressly incorporated herein by reference in their entirety and for all purposes.

STATEMENT OF GOVERNMENT SUPPORT

This invention was made with government support under Award No. GM18360 awarded by the National Institute of Health and Department of the Army Medical Defense Command Award No. DAMD1718014. The Government has rights in this invention.

BACKGROUND OF THE INVENTION

1. Field of the Invention

This invention relates generally to the field of detecting hazardous chemicals and chemical analysis, to include portable automatic sensing devices. More particularly, the present invention relates to methods, compositions, devices and kits thereof useful in the detection of chemical agents, insecticides and other acetylcholinesterase (AChE) inhibitors, modifiers and ligands.

2. Background Information

Acetylcholinesterase (AChE), a serine hydrolase in the α/β-fold hydrolase protein superfamily, terminates nerve signals by catalyzing hydrolysis of the neurotransmitter acetylcholinesterase at a diffusion-limited rate. A number of nerve toxins, including insecticides and organophosphates, act through binding to and inhibiting AChE.

Organophosphorus and organosulfur compounds, are used extensively in insecticides and are highly toxic to many organisms including humans. Insecticide residues are found in soil and groundwater, and the detection of these residues is important for their elimination from the environment and to protect the health of both humans and animals. Organophosphorus compounds are also used in nerve agents, such as sarin, phosphine, soman, and tabun, for chemical warfare purposes.

These agents are some of the most potent toxic agents and are specific inhibitors of acetylcholinesterase (AChE).

Acetylcholine is an essential neurotransmitter that affects parasympathetic synapses (autonomic and CNS), sympathetic preganglionic synapses, and the neuromuscular junction (see, e.g., Taylor et al., in *Basic Neurochemistry*, 5th ed., 1993, (Siegal et al., eds.), Chapter 11, pp. 231-260, Raven Press, New York, N.Y.). Hydrolysis of acetylcholine by acetylcholinesterase, present in nervous tissue, normally limits the duration of action function. Organophosphate (e.g., Malathion, Parathion, Diasinon, Dursban) and carbamate (e.g., Sevin, Furadan) insecticides exert their toxicity by inhibiting the action of acetylcholinesterase and thereby causing a pronounced cholinergic response (Arron et al., Insecticides: Organophosphate and Carbamates in *Goldfrank's Toxicologic Emergencies*, 1994, (Goldfrank et al., eds.), Appleton & Lange, Norwalk, Conn.). Enzyme inhibition is the consequence of phosphorylation (organophosphates) or carbamylation (carbamates) of the cholinesterase-active site serine residue. The resulting phosphoroyl-serine bond is stable; therefore, enzyme inhibition is physiologically irreversible, whereas the carbamyl-serine bond undergoes spontaneous hydrolysis with regeneration of enzyme activity (24-48 h). For this reason and because of poor CNS penetration, carbamate insecticide neurotoxicity is less severe and of shorter duration than that for the organophosphates (*Tietz Textbook of Clinical Chemistry*, 1999, (Burtis et al., eds.), W. B. Saunders Company, Philadelphia, Pa.).

Excess synaptic acetylcholine stimulates muscarinic receptors (peripheral and CNS) and stimulates but then depresses and paralyzes nicotinic receptors. The CNS neurotoxic effects include restlessness, agitation, lethargy, confusion, slurred speech, seizures, coma, cardiorespiratory depression, or death.

The need for the reliable determination of these cholinesterase inhibitors has led to the development of a number of sophisticated instrumental methods, mostly involving the use of gas and liquid chromatography and mass spectrometry. Also a number of liquid phase chemiluminescence procedures have been developed for the determination of inorganic and organic species mostly utilizing the luminol and peroxyoxalate reactions. See Robards K. and Worsfold P. J., Anal Chem Acta (1992) 266:147.

These traditional methods are not practical for individual use as the methods are time consuming and complicated and the instruments utilized are expensive, non-portable and require high maintenance. Additionally, the measurement of nerve agents in mixtures with these traditional methods requires cumbersome extraction and manipulation procedures.

Thus, biosensors were developed as an alternative to the traditional gas and liquid chromatography and mass spectrometry technology. Generally, biosensors include those which are enzyme-based and bioaffinity-based. An enzymatic biosensor uses an enzymatic or metabolic process to detect a reaction product which occurs between an incoming substrate and an immobilized enzyme. A bioaffinity sensor relies on a biological binding event of a target substance.

Many existing methods for the detection of organophosphates and cumulative inhibition of cholinesterases lack sensitivity since they are based on inhibition of basal activities rather than accumulation of the inhibitory conjugate. Basal activities vary substantially between subjects resulting in inconsistency in present assays.

Existing monitoring methods routinely require expensive laboratory procedures involving sample transport or preparations of samples for assay.

Rapid analysis of toxic materials in the areas of food and water analysis, environmental monitoring, and in industrial settings is a problem that continues to exist and is currently addressed by time-consuming, expensive methods or by techniques that may be described as inadequate.

Many problems associated with exposure to toxic materials could be avoided or minimized by a detection procedure which gives near "real-time" indication of the presence of toxic gases. Equally important are the characteristics of economy, small size, and ease of use for the successful application of such devices.

Accordingly, there is a need for a method of detecting, quantifying, and evaluating hazards which provides for early detection and which can detect low levels of toxic materials. The present invention satisfies this need, as well as others.

SUMMARY OF THE INVENTION

The present invention overcomes one or more of the drawbacks in the prior art by providing compositions and methods for their use in the detection of specific inhibitors, modifiers, or ligands of acetylcholinesterase (AChE). Disclosed are methods for the preparation and use of labeled AChE and labeled AChE inhibitory conjugate compositions which are useful in detecting accumulation of toxic materials, which include but are not limited to, organophosphates, insecticides, nerve agents, such as sarin, phosphine, soman, and tabun, and other materials used for chemical warfare purposes. Also disclosed are methods for the use of labeled AChE and labeled AChE inhibitory conjugate compositions in a variety of areas, including the detecting of toxic materials in biological samples, the areas of food and water analysis, environmental monitoring, and in industrial settings. Embodiments are disclosed which describe methods for making and using labeled AChE and labeled AChE inhibitory conjugate compositions comprising fluorescing compounds, including but not limited to, dimethoxyphosphoryl and diethoxyphosphoryl labels.

In one embodiment of the invention, methods are disclosed for measuring accumulation of inhibitory conjugates comprising labeled AChE and an inhibitor, modulator or ligand (i.e., cognate partner). In a related aspect, such methods may comprise contacting a sample suspected of containing such cognate partners with labeled AChE in order for labeled AChE binding to occur between cognate partners in the sample and the enzyme. In a further related aspect, conjugated and unconjugated AChE may be separated by chromatographic methods. For example, such chromatographic methods may include, but are not limited to, capillary electrophoresis.

In another embodiment, the conjugated and unconjugated, labeled AChE are detected and differentiated by fluorochromic emission shift, where conjugated AChE shows a detectable shift in emission signal. In a related aspect, the shift in emission is a Stokes' shift upon conjugate formation.

In a related aspect, the cognate partner is an inhibitor, where the inhibitor may be designated as a carbamylating inhibitor or a phosphorylating inhibitor. In a further related aspect, the inhibitor may be an insecticide or an organophosphate.

In another related aspect, the presence of the cognate partner is estimated by determining the ratio of conjugated to unconjugated AChE.

In another embodiment, the sample may be obtained from the atmosphere, soil, water, industrial sites or environmental sites. Further, the sample may be biological or non-biological. In a related aspect, a biological sample may include, but is not limited to, the integumentary system, sputum, feces, blood, urine, plasma, lacrimal secretions, cerumen, and semen.

In one embodiment, the AChE is labeled on at least one site. In a related aspect, the AChE is labeled at multiple sites. In a further related aspect, the at least one label is peripheral to the active center of the AChE.

In one embodiment, a device comprising AChE is envisaged, where the AChE is compartmentalized in a mobile or stationary phase. In a related aspect, the stationary phase is a chip. In another related aspect, the mobile phase is a suspension.

In one embodiment, the device is a biosensor for analyzing a sample for at least one organophosphorous, nerve agent and/or insecticide, where at least one enzyme is immobilized on or within the device. In a related aspect, the immobilized enzyme is either covalently or non-covalently bound to the device. In a further related aspect, the biosensor is divided into multiple zones, where each zone differentiates between one or more organophosphorous, nerve and/or insecticide agents.

In another embodiment, the present invention also provides kits which contain the present labeled AChE for use in the present identification method.

In another embodiment, a labeled AChE composition comprising at least one fluorophore located peripherally to the active center of the AChE, where the at least one fluorophore possesses an emission signal that shows a Stokes' shift upon conjugate formation. In a related aspect, the fluorophore comprises a dimethoxyphosphoryl label or a diethoxyphosphoryl label.

In another embodiment, a labeled AChE molecule comprises at least one fluorophore on at least one site present at the periphery of the active site of the enzyme, wherein the at least one site is selected from the group consisting of residues 76, 81, 84, 124, 262 and 287 of AChE or equivalents thereof.

Exemplary methods and compositions according to this invention, are described in greater detail below.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Before the present compositions and methods are described, it is understood that this invention is not limited to the particular methodology, protocols, and reagents described as these may vary. It is also to be understood that the terminology used herein is for the purpose of describing particular embodiments only, and is not intended to limit the scope of the present invention which will be described by the appended claims.

It must be noted that as used herein and in the appended claims, the singular forms "a", "an", and "the" include plural reference unless the context clearly dictates otherwise. Thus, for example, reference to "a subject" includes a plurality of such subjects, reference to "an enzyme" includes one or more enzymes and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the proteins, compounds, and methodologies which are reported in the publications which might be used in connection with the invention. Nothing herein is to be construed as an admission that the invention is not entitled to antedate such disclosure by virtue of prior invention.

Figure 6:
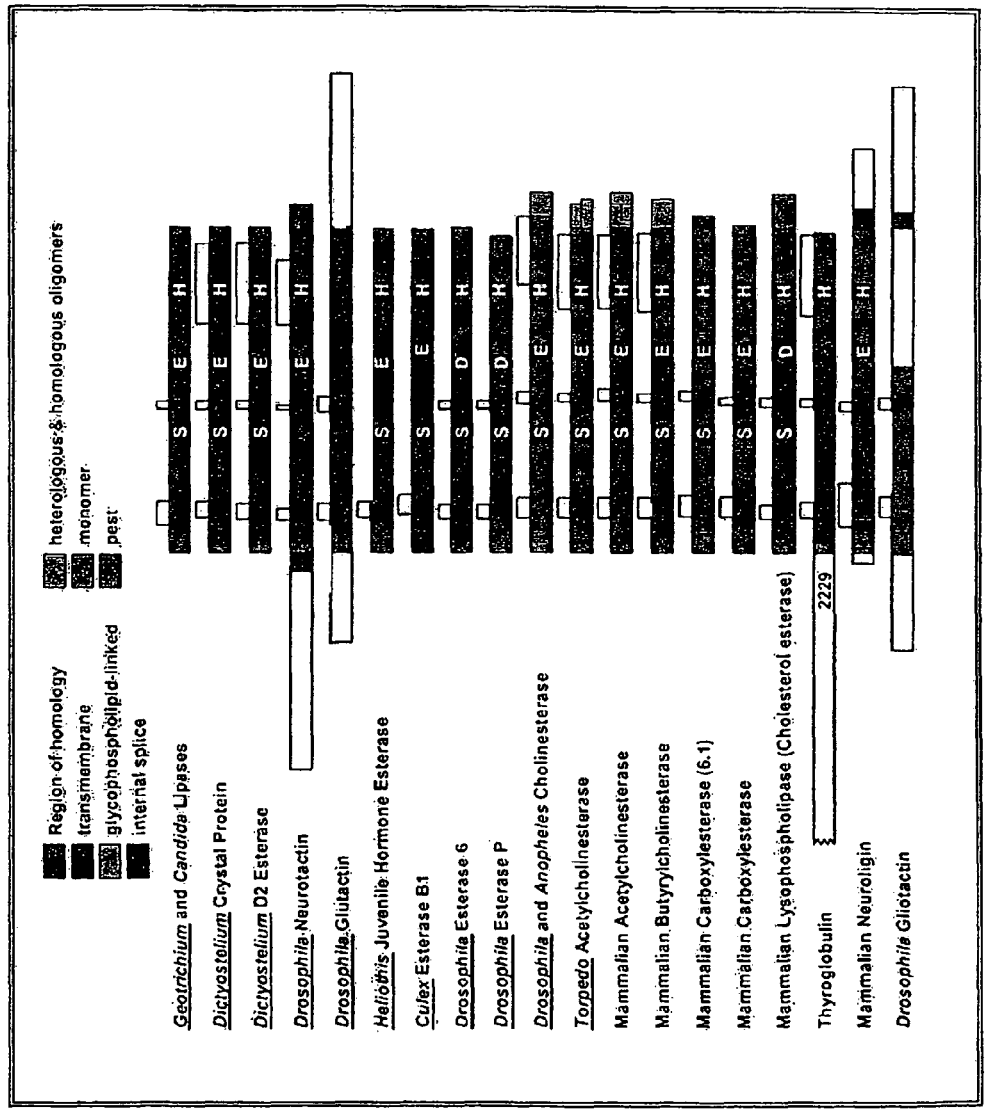
FIG. 6 shows an illustration showing regions of homology between AChE and various enzyme species.

As used herein acetylcholinesterase (AChE) means a serine hydrolase in the α/β fold hydrolase protein superfamily which terminates nerve signals by catalyzing the hydrolysis of the neurotransmitter acetylcholine. In one embodiment, AChE is from mouse (e.g., but not limited to, Accession Nos. 1maa (SEQ ID NO: 1) and 1mah (SEQ ID NO: 2). In a related aspect, the mutagenized residues of AChE as envisaged in the instant invention are denoted by the wild type residue, followed by the residue number (based on, for example the Accession Numbers, supra), with the mutated residue last (i.e., cysteine, "C"). For example, based on Accession No. 1maa IMAAA (SEQ ID NO: 1), conversion of residue 81 (i.e., Glu or E) to cysteine (or C) would be denoted as follows: E81 C. Corresponding structures on equivalent AChE molecules may be determined by alignment of homologous regions (see, e.g., FIG. 6 and Cygler et al., Protein Sciences (1993)2,366-382.

Equivalents of AChE may include, but are not limited to, *Candida* lipase (Acc. No. CAD86495, SEQ ID NO: 3), *Dictyostelium* crystal protein (Acc. No. CAA36702, SEQ ID NO: 4), *Drosophila* glutactin (Acc. No. S12519, SEQ ID NO: 5), *Heliothis* juvenile hormone esterase (Acc. No. P12992, SEQ ID NO: 6), *Culex* esterase B1 (Acc. No. A35986, SEQ ID NO: 7), *Drosophila* esterase P (Acc. No. AAD39965, SEQ ID NO: 8), *Drosophila* esterase P (Acc. No. B34089, SEQ ID NO: 9), *Drosophila* cholinesterase (Acc. No. A25363, SEQ ID NO: 10), *Torpedo* acetylcholinesterase (ACC. No. ACRYE, SEQ ID NO: 11), mammalian acetylcholinesterase (e.g., homo sapiens, ACC. No. AAA53473, SEQ ID NO: 12), mammalian butyrylcholinesterase (e. g., homo sapiens, Acc. No. AAH18141, SEQ ID NO: 13), mammalian carboxylesterase (6.1) (e. g., rattus norvegicus, Acc. No. P16303, SEQ ID NO: 14). In a related aspect, derivatives, fragments and variants of these AChE equivalents are also envisaged for the methods, compositions and devices of the present invention. (See, also e.g., FIG. 6 and Cygler et al., see above).

In one embodiment, mutants can be prepared by site-directed mutagenesis (or evolution methods, see e.g., Devlin et al., Science (1990) 249:404-406; and Scott & Smith, Science (1990) 249:386-390) using a conventional oligonucleotide directed in vitro mutagenesis system such as that described by Eckstein et al., Nucleic Acids Research (1985) 13:8749-8785. (See also, U.S. Pat. No. 6,001,625). Other conventional PCR techniques known in the art may be used.

In one embodiment, the selection of residues for replacement is based on a molecular model, using the crystal structure of AChE published by Sussman, et al. on an Evans and Sutherland PS390 platform with Biosym software.

As used herein, "cognate partner," including grammatical variations thereof, means a molecule that stereoselectively binds within the active site of AChE. For example, a ligand (e.g., acetylcholine), modulator (e.g., galantamine) or inhibitor (e.g., organophosphates) of AChE would be considered a cognate partner.

The instant invention is a sensitive method for the detection of AChE ligands, modulators and inhibitors using fluorescent labeled forms of AChE. The AChE of the present invention is labeled at sites peripheral to the active center with a fluorophore whose emission signal shows a large Stokes' shift upon binding of ligands. The attached fluorophore does not interfere with ligand binding, so the high affinity for inhibitors, modifiers or ligands seen in the native enzyme is maintained. The labeled AChE of the present invention can be used to detect interaction with inhibitors, modifiers and ligands. This is particularly useful for the detection of organophosphates such that insecticides or nerve agents and provides a method to determine if the concentrations of a substance present in the atmosphere or ground are sufficient to inhibit AChE.

After a dye molecule has been electronically excited due to absorption of light, it may almost instantaneously emit light. This very fast process occurring on the nanosecond time scale ($10^{-9}$ sec) is called fluorescence. A fluorescence dye is characterized by its spectral characteristics (excitation and emission spectra, lex and lem respectively), its quantum yield (QY) and its fluorescence lifetime (t).

The spectral characteristics of fluorescence dyes depend strongly on their molecular backbone. For absorption and emission in the UV, near the visible spectral range, at minimum, a system of conjugated double bonds is needed. The wavelengths of absorption and emission are simply stated as shifted towards red or longer wavelengths. Additional electron donating substituents are necessary for the spectral characteristics of the dye to finally occur in the visible spectrum of light (400-700 nm), which is called the bathochromic shift.

The emitted light occurs normally at a longer wavelength with respect to the absorbed light due to a loss in energy while the dye molecules remain in their electronically excited state. This so-called Stokes' shift makes the maximum emission occur at a few or up to several tens of nanometers ($10^{-9}$ m) red-shifted with respect to the absorption maximum. These spectral properties of a dye are widely used for the identification of differently labeled probes. In a related aspect, the fluorophores of the present invention exhibit large Stokes' shift (i.e., the difference in wavelength between the excitation wavelength and the emission wavelength).

One of the most important properties of a fluorescence dye is the quantum yield (QY). The quantum yield is the ratio of emitted light to the light absorbed prior to the observed fluorescence. Hence the quantum yield is a measure of the efficiency of fluorescence, which is concurring with other so-called dark processes. The higher the quantum yield of a fluorescence dye the better it can be observed.

Due to the quantum nature of fluorescence, the emission of light from each molecule occurs arbitrarily after its excitation. In other words, the dye molecules remain in the electronically excited state for a very short but random time span. Nevertheless the statistics of emission follows a known model, which in the simplest case is an exponential decay. This well known kinetic law contains a time constant called fluorescence lifetime, mostly abbreviated as t, which is characteristic for the given dye and may be used for its identification.

Fluorescence lifetime and the closely related quantum yield may strongly depend on the molecular environment of the individual dye molecule, such as the surrounding solvent or the local pH. Therefore a change of these properties indicates a change of the local environment of the dye molecules. Close investigations of this phenomenon have revealed several well-defined processes, often referred to as quenching, which can be used for switching the dye properties, allowing for the development of intelligent probes (GenePin).

As used herein, "hypsochromic," including grammatical variations thereof, means a shift of a spectral band to higher frequency or shorter wavelength upon substitution or change in medium (e.g., solvent). It is informally referred to as a blue shift, and is opposite to bathochromic shift.

Sensitivity of assays and devices envisaged by the present invention is high, because the method of evaluating the presence of a conjugate (e.g., a labeled AChE-inhibitory conjugate) is based on detection with high quantum yield fluorophores. In one embodiment, the label is acrylodan.

Fluorescence emission of acrylodan is exquisitely sensitive to the dielectric constant of the solvent. In general, the fluorescence emission spectrum of acrylodan shifts toward the red (bathochromic), and the quantum yield decreases as the polarity of solvent increases (20, 40-42). This sensitivity to solvent polarity arises from the interaction of the excited state of acrylodan with its surrounding solvent. The excited state is more polar than the ground state and, as such, will interact with a polar solvent so as to align solvent dipoles. This alignment lowers the energy of the excited state and causes the red shift of the emission spectrum. Hence, an acrylodan-labeled enzyme with an emission maximum of 510-525 nm likely reflects exposure of the side chain to solvent (20, 42). On the other hand, acrylodan emission maxima in the range of 475-500 nm likely reflect solvent exclusion and a more hydrophobic environment surrounding the fluorophore. For example, the time course of $TFK^+$ reaction with acrylodan-E84C (FIG. 3) reveals a large spectral shift from 477 to 512 nm, indicating acrylodan conjugated at this position has moved to a more hydrophilic environment with $TFK^+$ bound. The large spectral shift yields a clear isoemissive point (i.e., the wavelength at which the intensity of emission of a sample does not change during a chemical reaction or physical change. The term derives from the Greek word for 'same luminescence'), which arises when only two distinct emitting species are present, in this case the free enzyme and the $TFK^+$ conjugate.

As used herein, "accumulation of conjugates," including grammatical variations thereof, means continuous increase in the number of AChE molecules bound (i.e., combine by chemical action) by a ligand, modulator or inhibitor.

As used herein, "conditions sufficient for binding of an inhibitor to the enzyme" includes, but is not limited to, contacting a labeled AChE (or equivalents thereof) comprising a carrier (e.g., bovine serum albumin) in an appropriate buffer (e.g., sodium phosphate buffer, pH 7.0) with various concentrations of cognate partners, for example between about 0.05 mins to about 0.1 mins, about 0.1 mins to about 0.5 mins, about 0.5 mins to about 1 min, about 1 min to about 2.5 mins, about 2.5 mins to about 3 mins, about 3 mins to about 4.5 mins, about 4.5 mins to about 5.5 mins, about 5.5 mins to about 7 mins, about 7 mins to about 10 mins, about 10 mins to about 15 mins, about 15 mins to about 20 mins, or about 20 mins to 25 mins, at about 15° C. to about 20° C., about 20° C. to about 25° C., about 25° C. to about 30° C. to about 32° C., about 32° C. to about 37° C., about 37° C. to about 40° C. or about 40° C. to about 45° C.

As used herein, "biological sample," including grammatical variations thereof, means materials obtained from living organisms. For example, such samples include, but are not limited to, an integumentary system sample, sputum, feces, blood, urine, plasma, lacrimal secretions, cerumen, and semen.

As used herein, "non-biological sample," including grammatical variations thereof means materials obtained from inanimate objects or non-living materials. For example, such samples include, but are not limited to, soil, water, air and environmental (e.g., walls, floors, furniture etc.) surfaces.

Methods are described which distinguish between various classes of organophosphates by analyzing the fluorescence shift of labeled-AChE of the present invention. In a related aspect, the AChE may be labeled with various fluorophores, including but not limited to, dimethoxyphosphoryl and diethoxyphosphoryl labels. In a further related aspect, fluorophores yield different emission maxima.

In one embodiment, the labeled AChE can be immobilized on a chip to detect cumulative AChE inhibition. In a related aspect, such a chip can serve as a remote sensor for inadvertent or planned contamination.

In general, the simplest biosensor for compounds as envisaged for the present invention comprises a material having AChE immobilized upon or within a stationary phase, secured upon a carrier such as plastic, glass, cloth, nylon, rubber, etc. Detection of cognate partners may be qualitatively determined by separation of conjugated enzyme from unconjugated enzyme. To test for cognate partners, the biosensor is exposed to the sample to be tested. Since the accumulation of conjugated-immobilized enzyme is substantially similar to that observed for the soluble form, only a short duration of exposure to the sample is required. In a related aspect, a shift in fluorescence indicates the presence of a conjugate.

In one embodiment, the biosensor may be washed to remove compounds and/or compositions which may cause interference since the immobilized enzyme does not leach and the cognate partner is irreversibly bound to the immobilized enzyme. An appropriate buffer may be applied to the material. In a related aspect, in the field of drugs and testing of samples, it will be preferred to apply detectable cognate partners providing optimal signal in an aqueous system.

In one embodiment, biosensors may be disposed after a single use or may be reused. The biosensor may be regenerated using a reagent to displace the cognate partner, e.g. fluoride salts. Accuracy of the biosensor is assured if it is recalibrated prior to use.

The present invention also provides kits. Such kits will contain a container means which contains the instant enzyme. The container means may be any suitable container, but will typically be a glass vial or jar, a plastic pack, etc. In one embodiment, the container means may be a foil or plastic pouch which contains the enzyme immobilized on a microtitre plate or a chip. For example, a method of immobilization may include, but is not limited to, the method as described in Taylor et al. (U.S. Pat. No. 5,192,507). In other embodiments, the container means may be a plastic, glass, or metal tube which contains the enzyme, and the tube may possess an inlet means at one end and an outlet means at the other end; this type of container means may be used as a column in a flow biosensor and may itself be contained in a second container means.

The kit may further comprise a negative control sample. Such a negative control sample will contain either no cognate partner or a very low amount of cognate partner. The kit may also comprise a positive control sample, which will comprise, typically, an amount of cognate partner which is equal to or greater than the amount of cognate partner which is considered a positive result. The kit may also contain chemicals, such as buffers or diluents, and sample handling means, such as pipettes, reaction vials, vessels, tubes, or filters.

In addition, the kit may comprise written instructions on a separate paper, or any of the container means, or any other packaging. These instructions will usually set forth the conditions for carrying out the detection method, such as mixing ratios, amounts, incubation times, etc., and criteria for evaluating the results of the method, including spectra charts.

The following examples are intended to illustrate but not limit the invention.

EXAMPLES

The following examples are to exemplify certain embodiments of the invention. Those of skill in the art should, in light of the present disclosure, appreciate that many changes can be made in the embodiments which are disclosed and still obtain a like or similar result without departing from the spirit and scope of the invention.

Materials and Methods

Inhibitors and Substrates-Acetylthiocholine iodide, 5,5'-dithiobis(2-nitrobenzoic acid) (Ellman's reagent), dithiothreitol, tacrine (9-amino-1,2,3,4-tetrahydroacridine hydrochloride hydrate), BW284c51, decamethonium, and edrophonium were purchased from Sigma. m-(N,N,N-trimethylammonio)trifluoromethylacetophenone (TFK$^+$) and (−)huperzine A were purchased from Calbiochem. Acrylodan was obtained from Molecular Probes (Eugene, Oreg.). Fasciculin 2 (purified from the venom of *Dendroaspis angusticeps*) was a gift of Dr. Pascale Marchot (University of Marseille, France). Drs. Yacov Ashani and Bhupendra P. Doctor (Walter Reed Army Research Center, Washington, D.C.) kindly provided 7-((methylethoxy) phosphinyl)-oxyl)-1-methylquinolinium iodide (MEPQ) and procainamide-linked Sepharose CL-4B resin. m-tert-Butyl trifluoromethylacetophenone (TFK$^+$) was synthesized as described (21) and kindly provided by Dr. Daniel Quinn, University of Iowa, Iowa City, Iowa. All other chemicals were of the highest grade commercially available.

Expression, Mutagenesis, and Purification of mAChE-Mouse AChE was produced by transfection of an expression plasmid (pCDNA3, Invitrogen, San Diego, Calif.) containing an encoding cDNA where the AChE sequence was terminated at position 548. The plasmid was transfected into HEK293 cells. Cells were selected with G418 to obtain stable producing cell lines, and AChE was expressed as a secreted soluble enzyme in serum-free media (20). Mutant enzymes were generated by standard mutagenesis procedures, and cassettes containing the mutation were subcloned into pCDNA3 (20). Nucleotide sequences of the cassettes were confirmed by double-stranded sequencing to ensure that spurious mutations were not introduced into the coding sequence. Affinity chromatography using (m-aminophenyl)trimethylammonium linked through a long chain to Sepharose CL-4B resin (Sigma) permitted one-step purification of AChE. From 4 to 6 liters of media, mutant and wild type enzyme were purified in quantities ranging between 5 and 25 mg, as described previously (22-24). Purity was ascertained by SDS-PAGE and by measurements of specific activity.

Assay of Catalytic Activity—The spectrophotometric method of Ellman was used (25), and kinetic constants for acetylthiocholine hydrolysis were determined by fitting the observed rates as described (26). Titration of active sites with known concentrations of the irreversible phosphorylating agent, MEPQ, was accomplished by the method of Levy and Ashani (27).

Acrylodan Labeling—Mutant enzymes were pretreated with 0.25 mM dithiothreitol for 30 min at room temperature to ensure reduction of the introduced cysteine. Excess dithiothreitol was removed by use of a G-50 Sephadex spin column (Roche Molecular Biochemicals) equilibrated in 10 mM Tris, 100 mM NaCl, 40 mM MgCl$_2$, pH 8.0. A volume of 1 µl of acrylodan at 100 times the enzyme concentration was slowly mixed with the enzyme to achieve a ~5-fold molar excess of acrylodan to mutant enzyme. Labeling was allowed to proceed for at least 12 h at 4° C., and unreacted acrylodan was removed by size exclusion chromatography using Sephadex G-25 (Amersham Pharmacia Biotech) in 0.1 M sodium phosphate buffer, pH 7. Concentrations of acrylodan-labeled enzyme were determined from the maximal absorbance found between 360 and 380 nm ($\epsilon$~16,400 M$^{-1}$ cm$^{-1}$). Stoichiometry of labeling of the various preparations, estimated from a comparison of enzyme concentration by protein (280 nm) to acrylodan (360-380 nm) absorbance, ranged as follows: L76C, 0.7-0.8; E81C, 0.79-1.0; E84C, 0.77-1.0; Y124C, 0.79-1.0; A262C, 0.69-0.85; and H287C, 0.82-0.88.

Specificity of labeling was assessed by comparison of areas under the fluorescence emission curves for acrylodan-treated mutant and wild type enzymes. Specific labeling for each mutant was as follows; L76C, 70-85%; E81C, 81-91%; E84C, 85-93%; Y124C, 83-90%, A262C, 80-90%; H287C, 70-76%.

Trifluoroacetophenone Inhibition—Picomolar amounts of enzyme in 0.01% bovine serum albumin in 0.1 M sodium phosphate buffer, pH 7.0, were reacted with TFK$^+$ in the absence of substrate. Inhibition was monitored by measuring residual enzyme activity by removal of aliquots during the course of the reaction. Bimolecular rate constants of inhibition were determined by nonlinear fit of the data (28).

$$\Delta F = \Delta F_{max}(E_t + I_t + K_d - \sqrt{(E_t + I_t + K_d)^2 - 4 E_t I_t})(2E_t)^{-1} \quad \text{(Eq. 1)}$$

$\Delta F$ and $\Delta F_{max}$ are the change and maximum change in fluorescence, respectively; $E_1$ is the total enzyme concentration, and $I_1$ is the total inhibitor concentration. Association of TFK$^+$ with acrylodan-labeled E81C and E84C was assessed from the kinetics of decrease in fluorescence at 470 and 477 nm respectively, following addition of a stoichiometric excess TFK$^+$ at several concentrations. Data were fitted to a single exponential approach to equilibrium.

Association and dissociation rate constants of edrophonium and BW286c51 with E81C and E84C AChEs were determined from changes in the tryptophan fluorescence using a stopped-flow spectrophotometer as described previously (29). Time-dependent decreases in tryptophan fluorescence were observed upon excitation at 276 nm by means of a 305 nm emission cut-off filter.

Example 1

Characteristics of Substrate Hydrolysis and Fasciculin 2 Inhibition

Crystallographic Structures and Solution Dynamics of the Acetylcholinesterase Complex—In the several crystal structures of AChE with conjugated or reversible bound ligands that have been studied, little evidence for change in enzyme conformation has been detected with a difference of less than a root mean square of 2 Å for the α-carbon backbone between the apoenzyme and the various complexes (4-6, 13, 14, 33-35, 44). Changes in side chain orientation occur most notably in the phenyl ring at position 337 for certain reversible complexes (34) and phenylalanine 297 when bulky organophosphates are conjugated to the active site serine (44). However, based on the multiple positions of the outer trimethylammonio moiety in decamethonium for mouse (6) and Torpedo crystal structures (34), some flexibility may exist particularly within the gorge itself. Brownian dynamics often require lining the radii of the attacking ligands or the residues lining the gorge in order to simulate the kinetics of diffusion-limited substrate access observed experimentally (45). Thus, all of crystal structures reported to date reveal a closed gorge with constrained dimension. The solution-based fluorescence studies reported herein provide the first physical evidence for localizing the ligand-induced conformational change to the Cys$^{69}$-Cys$^{96}$ Ω loop. This finding raises an interesting possibility that the unliganded enzyme exists in a rapidly converting conformational equilibrium between open and closed states, and both ligand binding and conditions of crystallization favor formation of a closed gorge state. In fact, analysis of the molecule dynamics of a solvated mouse AChE shows fluctuations yielding an average widening of the motions of the gorge, which may also be integral to the catalytic cycle of transacylation and deacylation during ester hydrolysis.

The cysteine-substituted enzymes show kinetics of acetylthiocholine hydrolysis similar to wild type enzyme (Table I and FIG. 2) suggesting that all mutant enzymes fold correctly despite the presence of the newly introduced cysteine. The $K_m$ value of E84C shows slightly less than a 4-fold increase, whereas the change in turnover rate, $k_{cat}$, is minimal. Similar changes in kinetic constants were observed previously for E84Q mAChE (28). Since $K_m$, in the diffusion-limited catalysis, depicts the initial encounter between substrate and enzyme, an increase in $K_m$ likely arises from the reduction of negative charge that electrostatically steers the cationic substrate into the active center gorge. Interestingly, a similar E81C mutation has little or no effect on substrate hydrolysis. Not all negatively charged residues around the active center appear to be involved equivalently in electrostatic steering.

Figure 2:
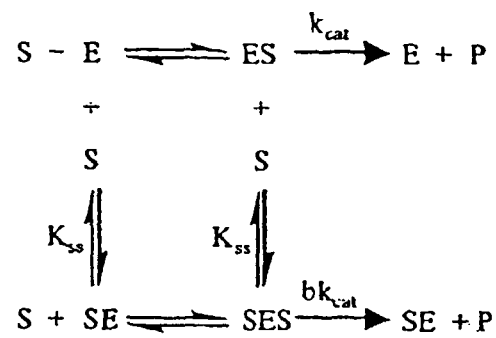
FIG. 2 shows a scheme showing combining of substrate at two discrete sites to form two binary complexes, ES and SE (where S is substrate; E is enzyme; and P is product). Only ES results in substrate hydrolysis. For simplicity, S is assumed to combine equally well with E and ES. The efficiency of substrate hydrolysis of the ternary complex SES, as compared with ES, is reflected in the value of the parameter, b, the relative catalytic turnover of the ternary complex (26).

Association and dissociation rates of fasciculin with A262C, H287C, and Y124C mutant enzymes were also found to be close to the rates of wild type enzyme (20). Fasciculin, at low concentrations, is also capable of associating with the mutant enzymes after acrylodan conjugation (FIG. 2). In addition, enzyme activity measurements of fasciculin-bound acrylodan conjugates show greater that 99% inhibition.

Example 2

Figure 3:
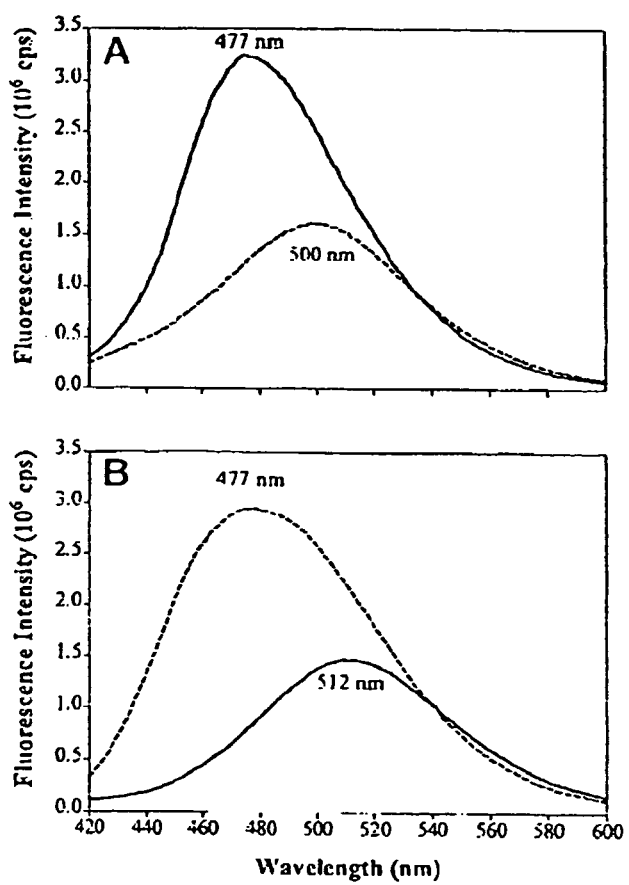
FIGS. 3A-B show fluorescence emission spectra of acrylodan-labeled Y124C(A) and E84C (B) AChE free in solution (dashed line) and complexed with fasciculin (solid line). A, for acrylodan-labeled Y124C, fasciculin produces a hypsochromic shift and enhancement of fluorescence quantum yield. The large shift for Y124C reveals a clear isoemissive point indicative of the two (free and fasciculin bound) species. Equivalent concentrations of enzyme (215 nM) were present for all conditions. The concentration of fasciculin was 215 nM. B, for acrylodan-labeled E84C, fasciculin produces a bathochromic shift and reduction of fluorescence quantum yield. Equivalent concentrations of enzyme (270 nM) were present for all conditions. The concentration of fasciculin was 800 nM.

Influence of Residue Modification of Inhibition by m-Trimethylammoniotrifluoromethylacetophenone TFK$^+$ binding to cysteine-substituted enzymes, both free and modified with acrylodan, was also examined (Table II). For E81C and E84C, the association rate constants ($k_{on}$) for TFK$^+$ were obtained from measurements of enzyme activity. Although positions 81 and 84 are both spatially removed from the TFK$^+$ binding site, $k_{on}$ for E84C is slightly slower than that for wild type enzyme. By contrast, E81C shows no difference in the kinetic constants. Conjugation of acrylodan, a neutral naphthalene derivative, with E84C reduces $k_{on}$ of TFK$^+$ 7-fold compared with unconjugated E84C, whereas conjugation of E81C with acrylodan only reduces $k_{on}$ of TFK$^+$ slightly. For acrylodan-labeled mutants, $k_{on}$ was measured from the time-dependent decrease of fluorescence signal (FIG. 3).

Influence of Residue Modification of Ligand Binding— The changes in emission spectra of acrylodan-labeled Ω loop residues 81 and 84 have been exploited to monitor ligand binding (Table II). Cysteine substitution and acrylodan conjugation at position 84, but not at position 81, affect ligand binding kinetics. Cysteine substitution at position 84 has little influence on catalytic parameters derived from steady-state catalysis (Table I).

TABLE I

Constants for acetylthiocholine hydrolysis by wild type and mutant mouse AChEs.*

| Enzyme | $K_m$ (μM) | $K_{SS}$ (mM) | b | $k_{cat}$ (10$^5$/min) | $k_{cat}/K_m$ (10$^9$/M-min) |
|---|---|---|---|---|---|
| WT[#] | 54 ± 16 | 14 ± 5 | 0.2 ± 0.07 | 1.6 ± 0.4 | 3.0 |
| Y124C[#] | 65 ± 17 | 20 ± 14 | 0.2 ± 0.09 | 1.4 ± 0.3 | 2.2 |
| H287C[#] | 58 ± 7 | 12 ± 6 | 0.2 ± 0.06 | 1.8 ± 0.2 | 3.1 |
| A262C[#] | 59 ± 4 | 11 ± 3 | 0.2 ± 0.04 | 1.6 ± 0.1 | 2.7 |
| L76C | 97 ± 19 | 17 ± 1 | 0.2 ± 0.03 | 1.8 ± 0.1 | 1.9 |

TABLE I-continued

Constants for acetylthiocholine hydrolysis by
wild type and mutant mouse AChEs.*

| Enzyme | $K_m$ (μM) | $K_{SS}$ (mM) | b | $k_{cat}$ ($10^5$/min) | $k_{cat}/K_m$ ($10^9$/M-min) |
|---|---|---|---|---|---|
| E81C | 57 ± 6 | 11 ± 1 | 0.2 ± 0.03 | 1.6 ± 0.1 | 2.9 |
| E84C | 190 ± 9 | 26 ± 2 | 0.2 ± 0.05 | 1.9 ± 0.4 | 1.0 |

*Data shown as means ± S.D. typically from three measurements. Data were fit to the Equation $v = (1 + b[S]/K_{SS})/V_{max}/(1 + [S]/K_{SS})(1 + K_m/[S])$, where [S] is substrate concentration, $K_{SS}$ is the substrate inhibition or activation constant, and b is the relative catalytic turnover of the ternary complex (12).
Data are from Boyd et al., J Biol Chem (2000) 275: 22401-22408.

The $K_m$ of E84C increases less than 4-fold compared with the wild type enzyme. By contrast, a similar substitution at position 81 has no effect of ATCh steady-state catalysis. Precise quantitation of these catalytic parameters for the acrylodan-conjugated enzyme is complicated by incomplete modification by acrylodan. However inhibitor association can be measured using the change in fluorescence signal (Table II).

TABLE II

Kinetic and equilibrium constants for reaction of enzymes with TFK+,
edrophonium, and BW284c51 in the presence of fluorescent (acrylodan) cysteine
labeling compound.*

| | TFK+ | | Edrophonium | | BW284c51 | |
|---|---|---|---|---|---|---|
| Enzyme | $k_{on}$ $10^9$M$^{-1}$min$^{-1}$ | $\frac{k_{on} \text{ WT}}{k_{on} \text{ mutant}}$ | $K_d$ nM | $\frac{K_d \text{ mutant}}{K_d \text{ WT}}$ | $K_d$ nM | $\frac{K_d \text{ mutant}}{K_d \text{ WT}}$ |
| Wild Type | 150 | | 250$^a$ | | 2.0$^a$ | |
| E81C | 150 | 1 | 260$^b$ | 1 | 2.6$^b$ | 1.3 |
| E81C-acrylodan | 94 | 1.6 | 640 | 2.6 | 6.9 | 3.5 |
| E84C | 93 | 1.6 | 550$^b$ | 2.2 | 35$^b$ | 18 |
| E84C-acrylodan | 13 | 11 | 6300 | 25 | 130 | 65 |

*Data are shown as means from two to three measurements. Individual determinations are within 35% of the mean. Rates for TFK$^+$ are calculated based on ratios of the hydrated and unhydrated ketone (21).
$^a$Data are from Radic et al. J Biol Chem (2001) 276: 4622-4633.
$^b$Equilibrium dissociation constants are derived from the ratio of $k_{off}/k_{on}$ using stopped-flow measurement of tryptophan quenching.

Reductions in binding kinetics were observed for several ligands (Table II) ranging between 1 or 2 orders of magnitude at position 84 but very little change at position 81. Although a portion of the reduction at position 84 is due to the cysteine substitution, acrylodan conjugation has a small, but significant (3-10-fold), influence on ligand binding. Even though both the 81 and 84 residues reside on the enzyme surface removed from the active center gorge, modification only at position 84 appreciably affects the energetics of ligand binding. The acrylodan moiety, whose dimension is slightly larger than the indole moiety of tryptophan, may impart steric restrictions to the region around the 84 site contributing to the energy cost in ligand binding. A small alteration in ligand binding energy (1.5-3.0 kcal/mol) is not unexpected if the conformation of the Ω loop plays a role in ligand binding.

Velan et al. (18) examined steady-state kinetics for a large number of Ω loop substitutions and truncations. Modification of Glu$^{84}$ and its neighboring residues was found to have limited effect on steady-state kinetics. Faerman et al. (19) inserted a cysteine at position 82 to pair with a second cysteine residing proximally in the body of the enzyme. Although it could not be firmly established that a disulfide bond formed, little change in kinetic parameters ($K_m$ and $k_{cat}$) was observed. Because of compensating contributions of the component primary constants, it is often difficult to correlate changes in steady-state kinetic parameters with structural perturbations. Our site-directed fluorophore labeling provides a physical assessment of the localized conformational change in the Ω loop. In cases where the fluorophore makes direct contact with the ligand, as the acrylodan-labeled Y124C and H287C with fasciculin, the energetic perturbations from substitution are larger, since complementarity of the binding site may be altered through the insertion of acrylodan side chain at the interface between the ligand and its binding site (20).

Acrylodan Modification at a Site Distal to the Active Center Core—The A262C modification was selected as a positional reference for a site distal to the active center. This residue is also located at the tip of the disulfide loop but is located ~30 Å away from the rim of the active center gorge. Crystallographic studies show this region to have a high temperature coefficient (B factor), indicative of substantial molecular motion of this surface residue. In fact, the position of this residue and its immediate neighbors is the only secured in crystal forms where proximity of the symmetry-related AChE molecule limits its movement in the crystal structure (6).

Acrylodan substitutions at this position show a long wavelength emission ($\lambda_{max}$=517 nm) indicative of exposure to a hydrophilic environment (Table III).

TABLE III

Fluorescence emission parameters of mouse AChE mutants
labeled with acrylodan in the presence of fasciculin.*

Acrylodan Emission Maxima (nm)

| Enzyme | No Fasciculin | Saturating Fasciculin | Chromic Shift (nm) | Relative Quantum Yield |
|---|---|---|---|---|
| L76C | 505 | 505 | 0 | 1.40 |
| E81C | 489 | 510 | 21 | 1.16 |
| E84C | 477 | 512 | 35 | 0.47 |
| $^a$Y124C | 500 | 477 | -23 | 1.78 |
| $^a$A262C | 517 | 517 | 0 | 0.97 |
| $^a$H287C | 524 | 507 | -17 | 5.0 |

*Data are shown as mean values of at least three determinations. Relative quantum yields were determined by comparison of areas of the fluorescence emission curves.
$^a$Data are from Boyd et al., J Biol Chem (2000) 275: 22401–22408.

Moreover, none of the ligands studied, whether they are covalently attached to the active center (TFK or alkylphosphates), reversibly bound to the active center (edrophonium), span between the active center and peripheral site (decamethonium and BW286c51), or bind only to peripheral site (fasciculin), affect the spectroscopic properties of acrylodan conjugated at site 262 (Tables III-VI).

TABLE IV

Fluorescence emission parameters of mouse AChE mutants labeled with acrylodan in the presence of covalent active site inhibitors.*

Acrylodan Emission Maxima (nm)

| Enzyme | Conjugated TFK⁰ | Chromic Shift (nm) | Relative Quantum Yield |
|---|---|---|---|
| L76C | 509 | 4 | 0.87 |
| E81C | 510 | 21 | 0.89 |
| E84C | 507 | 30 | 0.59 |
| Y124C | 478 | −22 | 1.15 |
| A262C | 517 | 0 | 0.97 |
| H287C | 524 | 0 | 0.90 |

Acrylodan Emission Maxima (nm)

| Enzyme | Conjugated TFK+ | Chromic Shift (nm) | Relative Quantum Yield |
|---|---|---|---|
| L76C | 511 | 6 | 0.92 |
| E81C | 510 | 21 | 0.89 |
| E84C | 512 | 35 | 0.52 |
| Y124C | 503 | 3 | 0.70 |
| A262C | 517 | 0 | 0.97 |
| H287C | 524 | 0 | 1.07 |

Acrylodan Emission Maxima (nm)

| Enzyme | Conjugated DDVP | Chromic Shift (nm) | Relative Quantum Yield |
|---|---|---|---|
| L76C | 503 | −2 | 1.27 |
| E81C | 510 | 21 | 0.19 |
| E84C | 496 | 19 | 0.39 |
| Y124C | 496 | −4 | 1.27 |
| A262C | 517 | 0 | 0.97 |
| H287C | 524 | 0 | 1.03 |

*Data are shown as mean values of at least three determinations. Relative quantum yields were determined by comparison of the areas of the fluorescence emission curves. Data for the unconjugated enzymes are found in Table III.

TABLE V

Fluorescence emission parameters of acrylodan-labeled mouse AChE mutants in the presence of reversible active site inhibitors.*

Acrylodan Emission Maxima (nm)

| Enzyme | Saturating Edrophonium | Chromic Shift (nm) | Relative Quantum Yield |
|---|---|---|---|
| L76C | 509 | 4 | 0.92 |
| E81C | 510 | 21 | 0.91 |
| E84C | 510 | 33 | 0.60 |
| Y124C | 500 | 0 | 0.79 |
| A262C | 517 | 0 | 0.97 |
| H287C | 524 | 0 | 1.13 |

Acrylodan Emission Maxima (nm)

| Enzyme | Saturating Huperzine A | Chromic Shift (nm) | Relative Quantum Yield |
|---|---|---|---|
| L76C | 511 | 6 | 0.86 |
| E81C | 510 | 21 | 0.88 |
| E84C | 510 | 33 | 0.55 |
| Y124C | 500 | 0 | 0.63 |
| A262C | 517 | 0 | 0.97 |
| H287C | 524 | 0 | 1.13 |

Acrylodan Emission Maxima (nm)

| Enzyme | Saturating Tacrine | Chromic Shift (nm) | Relative Quantum Yield |
|---|---|---|---|
| L76C | 509 | 4 | 0.87 |
| E81C | 510 | 21 | 0.91 |
| E84C | 510 | 33 | 0.45 |
| Y124C | 497 | −3 | 0.51 |
| A262C | 517 | 0 | 0.97 |
| H287C | 524 | 0 | 1.13 |

*Data are shown as mean values of at least three determinations. Relative quantum yields were determined by comparison of the areas of the fluorescence emission curves. Data for the unliganded enzymes are found in Table III.

TABLE VI

Fluorescence emission parameters of acrylodan-labeled mouse AChE mutants in the presence of bisquaternary ligands.*

Acrylodan Emission Maxima (nm)

| Enzyme | Saturating BW284c51 | Chromic Shift (nm) | Relative Quantum Yield |
|---|---|---|---|
| L76C | 508 | 3 | 1.13 |
| E81C | 510 | 21 | 0.98 |
| E84C | 512 | 35 | 0.47 |
| Y124C | 487 | −13 | 1.05 |
| A262C | 517 | 0 | 0.97 |
| H287C | 510 | −14 | 2.73 |

Acrylodan Emission Maxima (nm)

| Enzyme | Saturating Decamethonium | Chromic Shift (nm) | Relative Quantum Yield |
|---|---|---|---|
| L76C | 508 | 3 | 1.05 |
| E81C | 510 | 21 | 0.94 |
| E84C | 505 | 28 | 0.59 |
| Y124C | 465 | −35 | 1.85 |
| A262C | 517 | 0 | 0.97 |
| H287C | 517 | −7 | 1.76 |

*Data are shown as mean values of at least three determinations. Relative quantum yields were determined by comparison of the areas of the fluorescence emission curves. Data for the unliganded enzymes are found in Table III.

Figure 1:
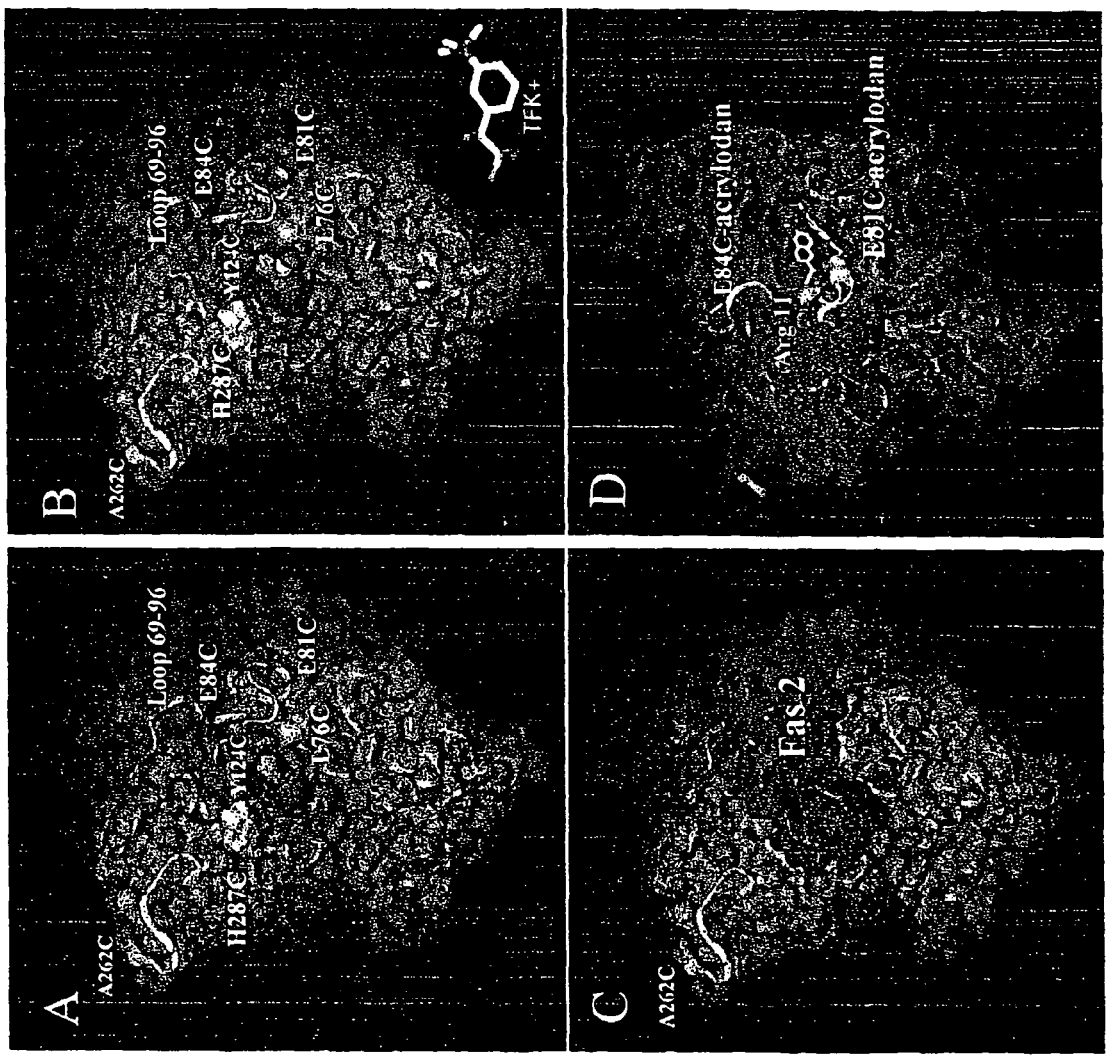
FIGS. 1A-D show locations of introduced cysteines for fluorophore modification. Residues 76, 81, and 84 are at the tip (76) and outer portion (81, 84) of the Ω loop. Residues 124 and 287 are on an opposing face of the gorge and make up part of the peripheral anionic site. Residue 262 is on a peripheral disulfide loop and in the crystal has a large thermal factor. A-D, Connolly surface representations of structure. A, unligated AChE (6); B, TFK$^+$ conjugated with AChE; note partial exposure of the white molecule TFK$^+$, at the base of the gorge (33); C, fasciculin 2 bound AChE at the mouth of the gorge (5); D, fasciculin 2 complex with AChE, rotated 90°. Acrylodan conjugated to E84C is shown in yellow; and acrylodan conjugated to E81C is shown in green. (Note in D the proximity between arginine 11 on Fas 2 and the acrylodan side chain at position 84).

This pattern indicates a lack of global conformational change affecting residue environments in a disulfide loop well removed from the active center (FIG. 1).

Residues Residing on the Active Center Gorge in Apposition with the Ω Loop—Residues 124 and 287 lie in close proximity to the Ω loop with H287C at the rim of the gorge and Y124C, residing just below the rim in the gorge interior (FIG. 1). The crystal structure of the complex shows fasciculin to "cap" these residues, hypsochromic shifts of acrylodan upon fasciculin binding (20). None of the reversibly bound active center ligands (edrophonium, huperzine, and tacrine) induce a spectral shift at position 124 or 287. However, modest quenching is observed at position 124 upon binding of these active center ligands. The bisquaternary ligands, which should approach or come in close apposition with these residues, cause significant hypsochromic shifts. The large shift for decamethonium at position 124 may reflect the ability of the cluster of aromatic residues to collapse around the methylene chain of decamethonium enlodged within the active center gorge. Crystallographic studies show one quaternary ammonium of decamethonium to be consistently positioned in the vicinity of Trp[84]; however, both the flexible side chain and the outermost quaternary group are found to assume multiple positions in the decamethonium-AChE complexes studied to date (6, 29).

Covalent inhibition of cationic trifluoroacetophenone (TFK$^+$) produces very little spectral shift of acrylodan at either position 124 or 287. This is consistent with the crystal structures where the trimethyl ammonio moiety of TFK$^+$ forms a cation –π interconnection with Trp$^{86}$, and the trifluoroacetophenone moiety forms a hemiketal bond with the active center serine 203 (33). However, the isosteric t-butyl congener (TFK$^0$) shifts the environment of residue 124 to that resembling a hydrophobic state. This difference suggests that the orientation of this hemiketal conjugate differs where the t-butyl group extends toward the gorge exit. TFK$^0$ inhibits the wild type enzyme 70-fold slower that TFK$^+$, presumably due to lack of cation-π interaction and slightly different ligand orientation (21). Alkyl phosphorylation with small alkyl groups also has little influence on the environment at position 124 (Table IV).

Ω Loop Substitutions—The residues modified, 76, 81 and 84, are all on the outer surface and do not form the inner gorge wall. Since residues 81 and 84 carry acidic side chains, they might be expected to show solvent exposure in the native enzyme and not be involved in the internal stabilization of the loop, as is evident in the crystal structure of the mouse enzyme (5, 6). In the absence of ligand, the spectra of the conjugated acrylodan moiety reveal different degrees of solvent exposure with the acrylodan at position 84 being the most protected in an hydrophobic environment, acrylodan at 81 being intermediate, and acrylodan at 76 being most exposed. Examination of the crystal structures of mouse enzyme revealed a surface cavity near the side chain of the 84 site (5, 6). The observed $\lambda_{max}$ likely reflects acrylodan buried in this surface cavity when conjugated to the 84 site (FIG. 1.).

The presence of fasciculin causes a large bathochromic shift of acrylodan fluorescence at both the 81 and 84 positions, as well as an increase in quantum yield of acrylodan at 76. The lack of shift in emission seen in quantum yield of acrylodan at the 76 position may simply reflect a balance between small environmental changes at 76 upon ligand binding by fasciculin. In the case of Glu$^{84}$, the bathochromic shift likely reflects Arg$^{11}$ of fasciculin loop I coming in van der Waals contact with the 84 side chain and displacing acrylodan into a more polar environment. However, an explanation of the bathochromic shift at position 81 requires a more involved analysis. Although 81 is removed from the fasciculin-binding site, fasciculin has a sufficient molecular dimension to restrict the Ω loop so that the entire loop freezes or closes upon fasciculin binding. Thus, fasciculin binding may confer strain on the α-carbon backbone structure of the Ω loop such that the acrylodan side chain at positions 81 and 84 becomes exposed to the hydrophilic environment. The fact that substitutions at both positions yielded acrylodan spectra with equivalent emission maxima after ligand binding suggests a conformational involvement of the entire loop.

Example 3

Figure 4:
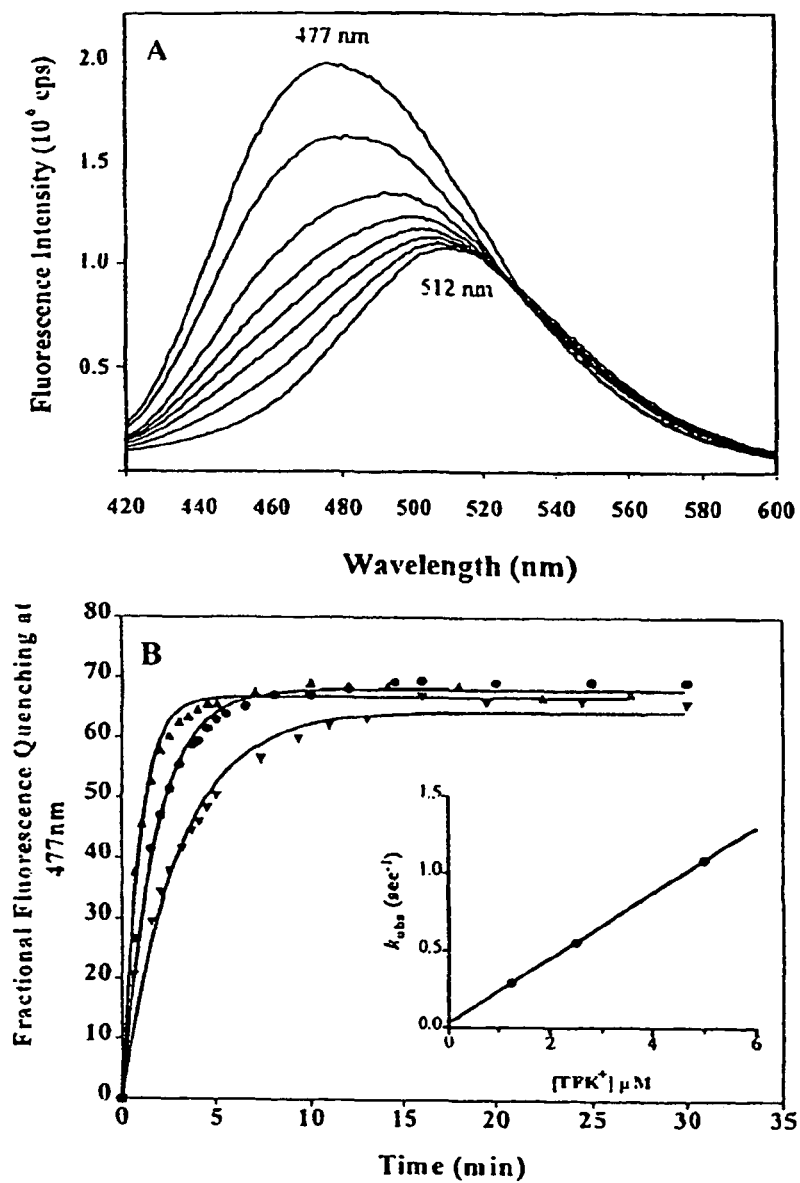
FIGS. 4A-B show association of TFK$^+$ with acrylodan-modified E84C AChE. A, fluorescence emission spectra of acrylodan-labeled E84C AChE following addition of excess TFK$^+$. TFK$^+$ produces a bathochromic shift and reduction of fluorescence quantum yield. The large chromic shift reveals a clear isoemissive point indicative of the two (free and TFK$^+$ bound) species. Initial enzyme concentration was 130 nM. Excess TFK$^+$ (1.25 µM) was added, and fluorescence spectra were recorded at the following times: 0, 1, 2.5, 4.3, 5.8, 7.4, 10.6 and 22 min. B, time course of the fluorescence changes. Initial acrylodan-modified E84C AChE concentration was 150 nM. Excess TFK$^+$ was added, and the decrease in fluorescence signal at 477 nm was monitored using an ISA Jobin Yvon-Spec Fluoromax fluorometer. The three TFK$^+$ concentrations were 1.25 (▼), 2.5 (●), and 5.0 (▲) µM. Control enzyme samples, to which buffer rather than TFK$^+$ was added, did not show decreases in fluorescence signals over the time intervals measured. The inset shows rates plotted as a function of TFK$^+$ concentration. $k_{on}$ for TFK$^+$ is calculated based on ratios of the hydrated and unhydrated ketone (21).
Figure 5:
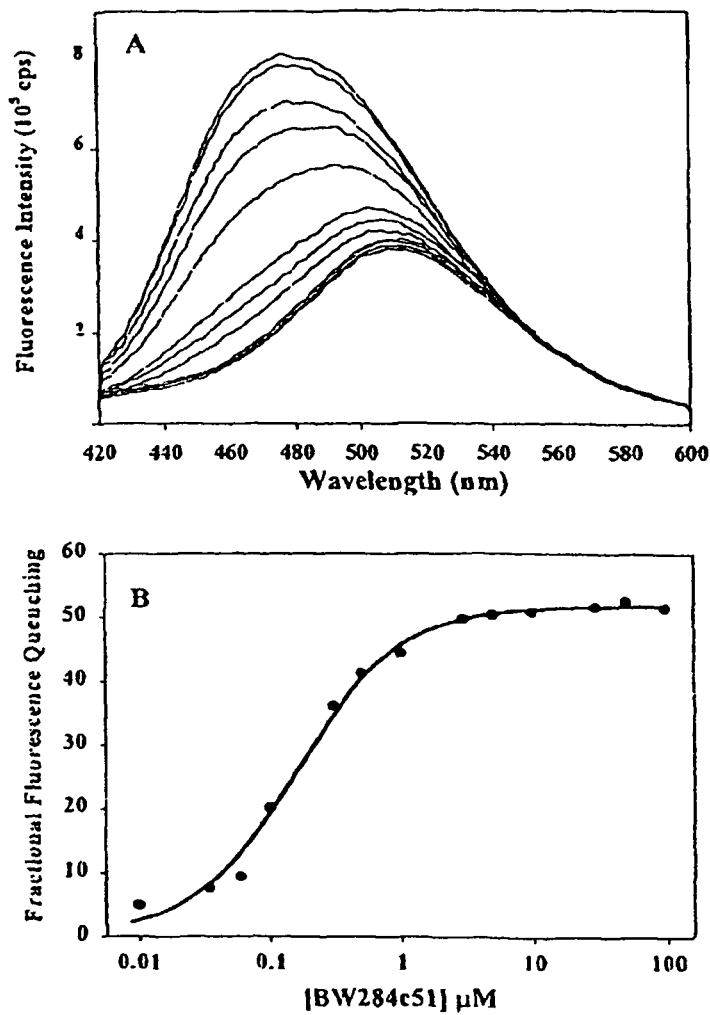
FIGS. 5A-B show association of BW284c51 with acrylodan-modified E84C AChE. A, fluorescence emission spectra of acrylodan-labeled E84C AChE following titration with BW284c51. BW284c51 produces a bathochromic shift and reduction of fluorescence quantum yield. Initial enzyme concentration was 70 nM. BW284c51 concentrations were 0, 0.01, 0.035, 0.06, 0.1, 0.3, 0.5, 1, 3, 5, 10, 30, 50, and 100 µM. B, the decrease in fluorescence emission curves is plotted as a function of BW284c51 concentration. $K_d$ is determined by fitting the data with Equation 1 as outlined below (EXAMPLES, Materials and Methods).

Influence of Residue Modification on Inhibition by Noncovalent Active Site Inhibitors A similar trend in inhibition kinetics was seen with noncovalent active site inhibitors such as edrophonium and BW286c51 (Table II). An increase over wild type $K_d$ of 2-fold occurs for edrophonium binding to E84C, and an 18-fold increase in $K_d$ is observed for BW286c51 binding. Similar increases in $K_d$ of edrophonium and BW286c51 were seen E84Q human AChE (18). By comparison, E81C showed no alterations in ligand binding constants. For acrylodan-labeled mutants, $K_d$ was measured from the fluorescence signals of an equilibrium titration (FIG. 4). Acrylodan-labeled E84C shows $K_d$ increases of 10-fold for edrophonium and 3-fold for BW286c51 as compared to unreacted E84C. For acrylodan-labeled E81C, only a slight increase in $K_d$ is seen for both ligands. The high concentration of acrylodan-labeled E81C required for equilibrium titrations precludes an accurate estimate of $K_d$ for high affinity ligands such as BW286c51.

Similar to fasciculin, small ligands that bind to the active center produce a similar strain. All of the small ligands, whether reversibly bound or covalently attached, elicit marked changes in acrylodan emission with the largest spectral shift seen for E84C, an intermediate value seen for E81C, and only small change observed for L76C. In each case the conformational change induced by the ligand causes the acrylodan to move into a region of higher dielectric constant, presumably being more solvent-exposed. The pattern is remarkably consistent among the ligands, and only the small organophosphate when conjugated induces a shift of smaller magnitude. A likely explanation for the observed conformational changes is that ligand binding to the active center induces gorge closure, which is mediated throughout the Ω loop. The strain placed on the α-carbon backbone upon gorge closure causes the side chains to shift positions and become exposed to a hydrophilic environment.

DeFari et al. (43) has noted that the peripheral site inhibitor, thioflavin T, when bound to AChE, shows a large enhancement of fluorescence. Simultaneous binding of an active center ligand and thioflavin T partially quenches the enhanced fluorescence of bound thioflavin T. Radic and Taylor (29) have observed that bound active center ligands cause a partial quenching of the native tryptophan fluorescence in AChE. Since these ligands lack the spectral overlap for fluorescence resonance energy transfer, the bound ligand is likely to influence the connectivity between aromatic residues present in the gorge, thereby influencing fluorescence quantum yields. Taken together, these studies suggest that ligands induce conformational changes in AChE giving rise to a gorge conformation collapsed around the bound ligand. The site-directed cysteine mutagenesis and fluorescence labeling studies herein suggest the involvement of particular resides on the Ω loop in this conformational change.

Example 4

Effect of Fasciculin on Acrylodan Fluorescence Emission

The peptide toxin, fasciculin, inhibits AChE by tightly capping the mouth of the active center gorge (FIG. 1) (11, 30-32). Table III shows changes in emission maxima of acrylodan-labeled AChE mutants in the presence of fasciculin. There is no discernible change in fluorescence emission of acrylodan-conjugated A262C (20), consistent with the position 262 being distal to the fasciculin-binding site. The large hypsochromic shifts seen at both the 124 and 287 positions reflect solvent exclusions and an increase in hydrophobicity experienced by the fluorophores in the gorge upon fasciculin binding (20). For the Ω loop mutant, L76C, fasciculin binding produces a 40% increase in quantum yield but no change in emission maximum. Bathochromic shifts are found at both the 81 and 84 positions, with position 84 producing a shift of larger magnitude (FIG. 2 and Table III).

Example 5

Effect of Covalently Conjugated Active Site Inhibitors on Acrylodan Fluorescence Emission Changes in emission maxima of acrylodan-labeled AChE mutants in the presence of conjugating trifluoroacetophenones are shown in Table IV. The trifluoroacetophenones inhibit the enzyme by conjugating to form a hemiketal at the active site serine without dissociation of leaving group (33). Both the isosteric neutral and cationic trifluoroketones (TFK$^o$ and TFK$^+$) produced no discernible changes in emission spectra of acrylodan conjugated at H287C and A262C, consistent with a fluorophore position distant from gorge base and hence not in direct contact with ligand. Remarkably, both TFK$^o$ and TFK$^+$ produce a substantial bathochromic shift (at least 30 nm) with acrylodan-E84C. The trifluoroketones also produce a spectral shift of intermediate value (20 nm) for E81C and a much smaller change (4-6 nm) for L76C. Interestingly, neutral TFK$^o$ produces a large 22 nm of hypsochromic shift with the Y124C acrylodan conjugate.

O,O-Dimethyl-O-(2,2-dichlorovinyl)phosphate, a smaller achiral organophosphonate, phosphorylates the active site serine of mAChE, with subsequent departure of the dichlorovinyloxy group (34, 35). The small and symmetrical dimethyl phosphoryl conjugate remaining at the active site serine might lead one to suspect very little perturbation, if any at all, in fluorescence spectra. Indeed, acrylodan conjugated at positions 124, 262, and 287 showed very little or no change in spectrum. However, bathochromic shifts at positions 81 and 84 were observed, although of smaller magnitude for E84C when compared with other ligands (Table IV).

Example 6

Effect of Noncovalent Active Site Inhibitors on Acrylodan Fluorescence Emission

Noncovalent active site inhibitors, such as edrophonium, tacrine, and huperzine, associate primarily with the choline subsite at the base of the active site gorge. Crystal structures of inhibitors bound to *Torpedo californica* AChE revealed that these ligands should have no direct contact with the conjugated fluorophore at all six cysteine-substituted sites (36, 37). Upon edrophonium, tacrine, or huperzine association, alteration of acrylodan emission maxima is undetectable for positions 124, 287, and 262 (Table V). However, as seen for other ligands, acrylodan conjugated at E84C surprisingly shows a bathochromic shift of 33 nm (from 477 to 510 nm) upon inhibitor binding. A change of smaller magnitude is seen in the case of acrylodan-L76C (from 505 to 509 nm) and acrylodan-E81C (from 480 to 510 nm) with noncovalent active site inhibitors. Ligand binding results in a common emission maximum ($\lambda_{max}$~510 nm) for acrylodan at the three Ω loop positions.

Example 7

Effect of Bisquaternary Inhibitors on Acrylodan Emission Spectrum

Extended bisquaternary inhibitors, such as BW286c51 and decamethonium, belong to a class of inhibitors that interact with two binding sites of AChE simultaneously (32, 38-39). The quaternary ammonium moiety on one end of the molecule associates with the Trp$^{86}$ residue that characterizes the choline-binding site, whereas the other end resides near Trp$^{286}$ at the active site gorge rim. Table VI shows changes in emission maxima of acrylodan-labeled AChE mutants in the presence of bisquaternary inhibitors. No changes are observed at position 262. By contrast, both decamethonium and BW284c51 caused a pronounced hypsochromic shift and increase in quantum yields with acrylodan conjugated at Y124C and H287C. Addition of decamethonium produced a hypsochromic shift of 35 nm at position 124, and a modest 7 nm shift at position 287. BW284c51 has a similar effect; for the Ω loop mutants, L76C, E81C, and E84C, bathochromic shifts of similar magnitude to the monoquaternary ligands were observed (Tables V and VI).

Example 8

Determination of the Presence of Potential Gaseous Cognate Partners in the Field Using a Portable Detection Device Containing Acrylodan-Labeled Mouse Acetylcholinesterase (Accession No. lMAAA)

A chip is configured to comprise multiple compartments containing various forms of labeled, immobilized acetylcholinesterase (AChE). Acrylodan-labeled mouse AChE is generated by the method as outlined in Shi et al. (J Biol Chem (2001) 276(45):42196-42204 and see above in Materials and Methods)). Alternatively, the mouse AChE is mutagenized by the method as outlined in U.S. Pat. No. 6,001,625 and labeled as outlined in Shi et al. (2001).

Picomolar amounts of labeled AChE in 0.01% bovine serum albumin and 0.01 M phosphate buffer (pH 7.0) are immobilized on a solid phase by the method as described in U.S. Pat. No. 6,406,876. The immobilized enzyme is then lyophilized as described in U.S. Pat. No. 5,354,654 and sealed under a gas permeable membrane. Prior to use, the enzyme is reconstituted by rehydration with an appropriate aqueous buffer. Alternatively, the enzyme is immobilized directly on a gas permeable resin and affixed to the chip surface (see, e.g., U.S. Pat. No. 4,619,897). In the latter system, the appropriate buffer system is added just prior to exposure to the deployment area.

The chip is configured for both standard, right-angled fluorescence detection or for epifluoresence (i.e., comprising windows for incident and emission of excitation wavelengths at 90° relative to the incident [excitation] light source and/or detection of emitted wavelengths at 180°).

The forms of immobilized AChE are as follows: acrylodan-labeled unconjugated AChE (comprising both single-site and multiple-site labeled enzymes, labeled at residues Leu$^{76}$, Glu$^{81}$, Glu$^{84}$, Tyr$^{124}$, Ala$^{262}$ and/or His$^{287}$), acrylodan-labeled conjugated AChE (comprising the labels as above and further comprising various organophosphates such as sarin, phosphine, soman, or tabun as positive controls), and unlabeled forms of both conjugated and unconjugated AChE.

The chip is deployed in an area suspected of containing one or more airborne organophosphate agents. The chip remains in the area for a sufficient time (under ambient temperature conditions) to allow for diffusion of the surrounding gases across the gas permeable membrane and to contact/interact with the immobilized AChE.

The chip is then removed from the area and placed in a device that can detect fluorescence (e.g., spectrofluorimeter). The fluorescence detected in compartments containing newly formed conjugates is compared with the fluorescence detected in the corresponding controls. Estimation of ratios of unconjugated to conjugated forms of the AChE is measured. Subsequent determination of an accumulation of conjugated AChE demonstrates the presence of one or more organophosphate agents in the deployment area.

All of the compositions and methods disclosed and claimed herein can be made and executed without undue experimentation in light of the present disclosure. While the compositions and methods of this invention have been described in terms of illustrative embodiments, it will be apparent to those of skill in the art that variations may be applied to the composition, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. Although the invention has been described with reference to the above examples, it will be understood that modifications and variations are encompassed within the spirit and scope of the invention.

REFERENCES

1. Cygler et al., Protein Sci (1993) 2:366-382.
2. Rosenberry T. L., Adv Enzymol Relat Areas Mol Biol (1975) 43-:103-218.
3. Quinn, D. M., Chem Rev (1997) 87:955-979.
4. Sussman et al., Science (1991) 253:872-879.
5. Bourne et al., Cell (1995) 83:503-512.
6. Bourne et al., J Biol Chem (1999) 274:2963-2970.
7. Ripoll et al., Proc Natl Acad Sci USA (1993) 90:5128-5132.
8. Tan et al., Biochemistry (1993) 32:401-403.
9. Wlodek et al., Biopolymers (2000) 53:265-27.
10. Shou et al., Proc Natl Acad Sci USA (1998) 95:9280-9283.
11. Eastman et al., J Biol Chem (1995) 270:19694-20399.
12. Radic et al., J Biol Chem (1995) 270:20391-20399.
13. Harel et al., Structure (1995) 3:1355-1366.
14. Kryger et al., Acta Crystallogr Sec D Biol Crystallogr (2000) 56:1385-1394.
15. Schrag et al., J Mol Biol (1993) 230:575-591.
16. Grochulski et al., J Biol Chem (1993) 268:72843-72847.
17. Grochulski et al., Protein Sci (1993) 3:82-91.
18. Velan et al., FEBS Lett (1996) 395:22-28.
19. Faerman et al., J Biol Chem (2000) 275:22401-22408.
20. Boyd et al., J Biol Chem (2000) 275:22401-22408.
21. Nair et al., Biochemistry (1994) 33:8566-8576.
22. Marchot et al., Protein Sci (1996) 5:672-679.
23. Berman et al., Proc Natl Acad Sci USA (1971) 68:395-398.
24. De la Hoz et al., Life Sci (1986) 39:195-199.
25. Ellman et al., Biochem Pharmacol (1961) 7:88-95.
26. Radic et al., Biochemisrty (1993) 32:12074-12084.
27. Levy et al., Biochem Pharmacol (1986) 35:1079-1085.
28. Radic et al., J Biol Chem (1997) 272:23265-23277.
29. Radic et al., J Biol Chem (2001) 276:4622-4633.
30. Redic et al., J Biol Chem (1994) 296:11233-11239.
31. Taylor et al., Annu Rev Pharmacol Toxicol (1994) 34:281-320.
32. Marchot et al., J Biol Chem (1993) 268:12458-12467.
33. Harel et al., J Am Chem Soc (1996) 118:2340-2346.
34. Wilson, I. B. (1960) in The Enzymes (Boyer, P. D., Lardy. H., and Myrback, K. eds.), (1960) Vol. 4, 2nd Ed., pp. 501-520, Academic Press, New York.
35. Wong et al., Biochemistry (2000) 39:5750-5757.
36. Harel et al., Proc Natl Acad Sci USA (1993) 90:9031-9035.
37. Raves et al., Nat Struct Biol (1997) 4:57-63.
38. Taylor et al., Biochemistry (1975) 14:1989-1997.
39. Taylor et al., Mol Pharmacol (1974) 10:93-107.
40. Lakowicz, J. R. (1999) Principles of Fluorescence Spectroscopy, 2nd Ed., pp. 185-210, Kluwer Academic Publishers and Plenum Publishing Corp., New York.
41. Lew et al., J Biol Chem (1997) 272:1507-1513.
42. Pendergast et al., J Biol Chem (1983) 258:7541-7544.
43. De Ferrai et al., J Biol Chem (2001) 246:23282-23287.
44. Millard et al., Biochemistry (1999) 38:7032-7039.
45. Tara et al., Biopolymers (1998) 46:465-474.
46. Tai et al., Biophys J (2001) 81:715-724.

What is claimed is:

1. A kit comprising an immobilized labeled acetylcholinesterase (AChE) comprising a fluorophore conjugated to at least one non-active site amino acid residue, wherein the at least one non-active site amino acid residue is an amino acid at a position selected from the group consisting of amino acid residue position 76, 81, and 84 of an AChE as set forth in SEQ ID NO: 1 or SEQ ID NO: 2, wherein the non-active site amino acid residue to which the fluorophore is conjugated is a wild type amino acid at the position or a non-wild type amino acid substituted in place of the wild type amino acid.

2. The kit of claim 1, wherein the fluorophore shows a Stokes' shift upon binding of a ligand to the labeled AChE.

3. The kit of claim 1, wherein the AChE is a recombinantly produced protein.

4. The kit of claim 1, wherein the non-wild type amino acid substituted at the position in place of the wild type amino acid to which the fluorophore is conjugated is a cysteine residue.

5. The kit of claim 1, wherein the fluorophore is an Acrylodan.

6. The kit of claim 1, wherein the AChE is capable of specifically binding to a non-reversible inhibitor.

7. The kit of claim 1, wherein the AChE further comprises and is specifically bound to an anti-AChE antibody.

8. The kit of claim 1, wherein the labeled AChE is immobilized on a microtitre plate or a chip.

9. The kit of claim 1, further comprising a positive control sample.

10. The kit of claim 9, wherein the positive control sample comprises an insecticide or a nerve toxin.

11. The kit of claim 9, wherein the control sample is a positive control sample comprising an organophosphate.

12. The kit claim 1, wherein the AChE inhibitor is a carbamylating inhibitor or a phosphorylating inhibitor.

13. The kit of claim 1, wherein the AChE inhibitor is a nerve toxin.

14. The kit of claim 1, wherein the AChE inhibitor is an insecticide.

15. The immobilized labeled AChE of claim 1, wherein the AChE inhibitor is an organophosphate.

* * * * *

SEQUENCE LISTING

```
<160> NUMBER OF SEQ ID NOS: 14

<210> SEQ ID NO 1
<211> LENGTH: 547
<212> TYPE: PRT
<213> ORGANISM: Mus musculus

<400> SEQUENCE: 1

Glu Gly Arg Glu Asp Pro Gln Leu Leu Val Arg Val Arg Gly Gly Gln
1               5                   10                  15

Leu Arg Gly Ile Arg Leu Lys Ala Pro Gly Gly Pro Val Ser Ala Phe
            20                  25                  30

Leu Gly Ile Pro Phe Ala Glu Pro Pro Val Gly Ser Arg Arg Phe Met
        35                  40                  45

Pro Pro Glu Pro Lys Arg Pro Trp Ser Gly Val Leu Asp Ala Thr Thr
    50                  55                  60

Phe Gln Asn Val Cys Tyr Gln Tyr Val Asp Thr Leu Tyr Pro Gly Phe
65                  70                  75                  80

Glu Gly Thr Glu Met Trp Asn Pro Asn Arg Glu Leu Ser Glu Asp Cys
                85                  90                  95

Leu Tyr Leu Asn Val Trp Thr Pro Tyr Pro Arg Pro Ala Ser Pro Thr
            100                 105                 110

Pro Val Leu Ile Trp Ile Tyr Gly Gly Gly Phe Tyr Ser Gly Ala Ala
```

```
                    115                 120                 125
Ser Leu Asp Val Tyr Asp Gly Arg Phe Leu Ala Gln Val Glu Gly Ala
130                 135                 140

Val Leu Val Ser Met Asn Tyr Arg Val Gly Thr Phe Gly Phe Leu Ala
145                 150                 155                 160

Leu Pro Gly Ser Arg Glu Ala Pro Gly Asn Val Gly Leu Leu Asp Gln
                165                 170                 175

Arg Leu Ala Leu Gln Trp Val Gln Glu Asn Ile Ala Ala Phe Gly Gly
            180                 185                 190

Asp Pro Met Ser Val Thr Leu Phe Gly Glu Ser Ala Gly Ala Ala Ser
        195                 200                 205

Val Gly Met His Ile Leu Ser Leu Pro Ser Arg Ser Leu Phe His Arg
    210                 215                 220

Ala Val Leu Gln Ser Gly Thr Pro Asn Gly Pro Trp Ala Thr Val Ser
225                 230                 235                 240

Ala Gly Glu Ala Arg Arg Arg Ala Thr Leu Leu Ala Arg Leu Val Gly
                245                 250                 255

Cys Pro Pro Gly Gly Ala Gly Gly Asn Asp Thr Glu Leu Ile Ala Cys
            260                 265                 270

Leu Arg Thr Arg Pro Ala Gln Asp Leu Val Asp His Glu Trp His Val
        275                 280                 285

Leu Pro Gln Glu Ser Ile Phe Arg Phe Ser Phe Val Pro Val Val Asp
    290                 295                 300

Gly Asp Phe Leu Ser Asp Thr Pro Glu Ala Leu Ile Asn Thr Gly Asp
305                 310                 315                 320

Phe Gln Asp Leu Gln Val Leu Val Gly Val Val Lys Asp Glu Gly Ser
                325                 330                 335

Tyr Phe Leu Val Tyr Gly Val Pro Gly Phe Ser Lys Asp Asn Glu Ser
            340                 345                 350

Leu Ile Ser Arg Ala Gln Phe Leu Ala Gly Val Arg Ile Gly Val Pro
        355                 360                 365

Gln Ala Ser Asp Leu Ala Ala Glu Ala Val Val Leu His Tyr Thr Asp
    370                 375                 380

Trp Leu His Pro Glu Asp Pro Thr His Leu Arg Asp Ala Met Ser Ala
385                 390                 395                 400

Val Val Gly Asp His Asn Val Val Cys Pro Val Ala Gln Leu Ala Gly
                405                 410                 415

Arg Leu Ala Ala Gln Gly Ala Arg Val Tyr Ala Tyr Ile Phe Glu His
            420                 425                 430

Arg Ala Ser Thr Leu Thr Trp Pro Leu Trp Met Gly Val Pro His Gly
        435                 440                 445

Tyr Glu Ile Glu Phe Ile Phe Gly Leu Pro Leu Asp Pro Ser Leu Asn
    450                 455                 460

Tyr Thr Thr Glu Glu Arg Ile Phe Ala Gln Arg Leu Met Lys Tyr Trp
465                 470                 475                 480

Thr Asn Phe Ala Arg Thr Gly Asp Pro Asn Asp Pro Arg Asp Arg Lys
                485                 490                 495

Ser Pro Gln Trp Pro Pro Tyr Thr Thr Ala Ala Gln Gln Tyr Val Ser
            500                 505                 510

Leu Asn Leu Lys Pro Leu Glu Val Arg Arg Gly Leu Arg Ala Gln Thr
        515                 520                 525

Cys Ala Phe Trp Asn Arg Phe Leu Pro Lys Leu Leu Ser Ala Thr Asp
530                 535                 540
```

Thr Leu Asp
545

<210> SEQ ID NO 2
<211> LENGTH: 543
<212> TYPE: PRT
<213> ORGANISM: Mus musculus

<400> SEQUENCE: 2

Glu Gly Arg Glu Asp Pro Gln Leu Leu Val Arg Val Arg Gly Gly Gln
1               5                   10                  15

Leu Arg Gly Ile Arg Leu Lys Ala Pro Gly Gly Pro Val Ser Ala Phe
            20                  25                  30

Leu Gly Ile Pro Phe Ala Glu Pro Pro Val Gly Ser Arg Arg Phe Met
        35                  40                  45

Pro Pro Glu Pro Lys Arg Pro Trp Ser Gly Val Leu Asp Ala Thr Thr
    50                  55                  60

Phe Gln Asn Val Cys Tyr Gln Tyr Val Asp Thr Leu Tyr Pro Gly Phe
65                  70                  75                  80

Glu Gly Thr Glu Met Trp Asn Pro Asn Arg Glu Leu Ser Glu Asp Cys
                85                  90                  95

Leu Tyr Leu Asn Val Trp Thr Pro Tyr Pro Arg Pro Ala Ser Pro Thr
            100                 105                 110

Pro Val Leu Ile Trp Ile Tyr Gly Gly Gly Phe Tyr Ser Gly Ala Ala
        115                 120                 125

Ser Leu Asp Val Tyr Asp Gly Arg Phe Leu Ala Gln Val Glu Gly Ala
    130                 135                 140

Val Leu Val Ser Met Asn Tyr Arg Val Gly Thr Phe Gly Phe Leu Ala
145                 150                 155                 160

Leu Pro Gly Ser Arg Glu Ala Pro Gly Asn Val Gly Leu Leu Asp Gln
                165                 170                 175

Arg Leu Ala Leu Gln Trp Val Gln Glu Asn Ile Ala Ala Phe Gly Gly
            180                 185                 190

Asp Pro Met Ser Val Thr Leu Phe Gly Glu Ser Ala Gly Ala Ala Ser
        195                 200                 205

Val Gly Met His Ile Leu Ser Leu Pro Ser Arg Ser Leu Phe His Arg
    210                 215                 220

Ala Val Leu Gln Ser Gly Thr Pro Asn Gly Pro Trp Ala Thr Val Ser
225                 230                 235                 240

Ala Gly Glu Ala Arg Arg Arg Ala Thr Leu Leu Ala Arg Leu Val Gly
                245                 250                 255

Cys Pro Pro Gly Gly Ala Gly Gly Asn Asp Thr Glu Leu Ile Ala Cys
            260                 265                 270

Leu Arg Thr Arg Pro Ala Gln Asp Leu Val Asp His Glu Trp His Val
        275                 280                 285

Leu Pro Gln Glu Ser Ile Phe Arg Phe Ser Phe Val Pro Val Val Asp
    290                 295                 300

Gly Asp Phe Leu Ser Asp Thr Pro Glu Ala Leu Ile Asn Thr Gly Asp
305                 310                 315                 320

Phe Gln Asp Leu Gln Val Leu Val Gly Val Val Lys Asp Glu Gly Ser
                325                 330                 335

Tyr Phe Leu Val Tyr Gly Val Pro Gly Phe Ser Lys Asp Asn Glu Ser
            340                 345                 350

Leu Ile Ser Arg Ala Gln Phe Leu Ala Gly Val Arg Ile Gly Val Pro
        355                 360                 365

```
Gln Ala Ser Asp Leu Ala Ala Glu Ala Val Val Leu His Tyr Thr Asp
        370                 375                 380

Trp Leu His Pro Glu Asp Pro Thr His Leu Arg Asp Ala Met Ser Ala
385                 390                 395                 400

Val Val Gly Asp His Asn Val Val Cys Pro Val Ala Gln Leu Ala Gly
                    405                 410                 415

Arg Leu Ala Ala Gln Gly Ala Arg Val Tyr Ala Tyr Ile Phe Glu His
            420                 425                 430

Arg Ala Ser Thr Leu Thr Trp Pro Leu Trp Met Gly Val Pro His Gly
        435                 440                 445

Tyr Glu Ile Glu Phe Ile Phe Gly Leu Pro Leu Asp Pro Ser Leu Asn
    450                 455                 460

Tyr Thr Thr Glu Glu Arg Ile Phe Ala Gln Arg Leu Met Lys Tyr Trp
465                 470                 475                 480

Thr Asn Phe Ala Arg Thr Gly Asp Pro Asn Asp Pro Arg Asp Ser Lys
                    485                 490                 495

Ser Pro Gln Trp Pro Pro Tyr Thr Thr Ala Ala Gln Gln Tyr Val Ser
            500                 505                 510

Leu Asn Leu Lys Pro Leu Glu Val Arg Arg Gly Leu Arg Ala Gln Thr
        515                 520                 525

Cys Ala Phe Trp Asn Arg Phe Leu Pro Lys Leu Leu Ser Ala Thr
    530                 535                 540

<210> SEQ ID NO 3
<211> LENGTH: 471
<212> TYPE: PRT
<213> ORGANISM: Candida parapsilosis

<400> SEQUENCE: 3

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                    85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                    165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205
```

```
Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe His His His His His His
465                 470

<210> SEQ ID NO 4
<211> LENGTH: 550
<212> TYPE: PRT
        <213> ORGANISM: Dictyostelium discoideum

<400> SEQUENCE: 4

Met Asn Lys Ile Ile Ile Leu Ile Ile Leu Leu Ser Phe Asp Ile
1               5                   10                  15

Ile Ser Ala Ala Lys Lys Phe Gly Arg Lys Gly Ile Arg Thr Leu Gly
            20                  25                  30

Asp Asn Glu Val Leu Leu Ser Asp Gly Ala Ile Arg Gly Thr Val Thr
        35                  40                  45

Asp Thr His Arg Val Phe Tyr Gly Ile Pro Phe Ala Arg Pro Pro Ile
    50                  55                  60

Asp Glu Leu Arg Tyr Glu Asp Pro Gln Pro Lys Pro Trp Ser Tyr
65              70                  75                  80

Val Arg Asp Gly Thr Lys Gln Arg Asp Gln Cys Ile Gln Asp Cys Lys
            85                  90                  95

Leu Gly Lys Gly Ser Cys Ser Glu Val Gly Thr Ser Glu Asp Cys Leu
        100                 105                 110
```

```
Tyr Leu Asp Val Phe Ile Pro Arg Thr Val Asn Pro Gly Ser Lys Val
            115                 120                 125

Pro Val Met Val Phe Ile Pro Gly Gly Ala Phe Thr Gln Gly Thr Gly
130                 135                 140

Ser Cys Pro Leu Tyr Asp Gly Leu Lys Phe Ala Asn Ser Ser Val Ile
145                 150                 155                 160

Val Val Asn Val Asn Tyr Arg Leu Gly Val Leu Gly Phe Leu Cys Thr
                165                 170                 175

Gly Leu Leu Ser Gly Asn Phe Gly Phe Leu Asp Gln Val Met Ala Leu
                180                 185                 190

Asp Trp Val Gln Glu Asn Ile Glu Val Phe Gly Gly Asp Lys Asn Gln
            195                 200                 205

Val Thr Ile Tyr Gly Glu Ser Ala Gly Ala Phe Ser Val Ala Ala His
            210                 215                 220

Leu Ser Ser Glu Lys Ser Glu Gly Lys Phe His Arg Ala Ile Leu Ser
225                 230                 235                 240

Ser Thr Pro Tyr Thr Val Gly Leu Lys Ser Gln Thr Val Ala Arg Gly
                245                 250                 255

Phe Ala Gly Arg Phe Ser Ser Lys Ile Gly Cys Asp Leu Glu Asp Ile
            260                 265                 270

Asp Cys His Arg Ser Lys Ser Pro Glu Glu Ile Leu Ala Ile Gln Lys
            275                 280                 285

Glu Leu Gly Leu Ala Ile Gly Asp Lys Ile Leu Asp Ala Phe Thr Ile
290                 295                 300

Trp Ser Pro Val Val Asp Gly Ile Asn Val Asn Glu Gln Pro Leu Thr
305                 310                 315                 320

Met Ile Lys Gln Gly Thr Thr His Asp Val Pro Thr Ile Ile Gly Asp
                325                 330                 335

Asn Gln Asp Glu Ala Ile Leu Phe Val Tyr Met Thr Tyr Lys Asn Val
                340                 345                 350

Val Ile Pro Ser Ser Tyr Arg Thr Met Val His Val Leu Phe Gly Ile
            355                 360                 365

Ala Asn Gly Asn Lys Val Leu Glu His Tyr Pro Leu Pro Gly Phe Leu
            370                 375                 380

Lys Asp Ser Arg Pro Ile Leu Ser Lys Leu Leu Thr Asp Tyr Leu Phe
385                 390                 395                 400

Arg Cys Pro Gly Arg Tyr His Val Ser Lys Ser Ala Gln Ala Asn Glu
                405                 410                 415

Ser Pro Ile Tyr His Tyr Gln Tyr Lys Gln Val Leu Ser Gly Gly His
            420                 425                 430

Ser Phe Glu Ala Cys Glu Gly Leu Val Cys His Gly Thr Glu Leu Pro
            435                 440                 445

Met Val Phe Asn Thr Tyr Glu Ser Ala Leu Asp Leu Asp Leu Glu Glu
450                 455                 460

Glu Glu Glu Glu Phe Ala Gly Gln Leu Asn Asn Tyr Phe Val Asn Phe
465                 470                 475                 480

Ile Lys Tyr Ser Asn Pro Ser His Pro Asn Gly Leu Pro Thr Pro Lys
                485                 490                 495

Val Trp Asn Pro Thr Thr Lys Thr Thr Asn Thr Ser Leu Val Met Lys
            500                 505                 510

Leu Gly Phe Glu Val Lys Asp Leu Ile Thr Asn Asp Pro Lys Cys Asp
            515                 520                 525

Leu Phe Asp Ser Leu Ser Tyr Asn Gly Tyr Thr Lys Asp Gln Asn Arg
530                 535                 540
```

```
Met Arg Lys Ser Lys Lys
545                 550

<210> SEQ ID NO 5
<211> LENGTH: 1023
<212> TYPE: PRT
<213> ORGANISM: Drosophila melanogaster

<400> SEQUENCE: 5

Met Lys Pro Leu Leu Val Leu Ala Leu Cys Gly Ala Gln Val His
1               5                   10                  15

Ala His Ser Val Gly Leu Arg Pro Asp Tyr Asn Asp Tyr Ser Asp Glu
                20                  25                  30

Asp Thr Arg Arg Asp Trp Leu Pro Glu Pro Leu Lys Pro Val Pro Trp
                35                  40                  45

Gln Ser Glu Thr Arg Tyr Ala Gln Pro Gln Glu Ala Val Val Gln Ala
        50                  55                  60

Pro Glu Val Gly Gln Ile Leu Gly Ile Ser Gly His Lys Thr Ile Ala
65                  70                  75                  80

Asn Arg Pro Val Asn Ala Phe Leu Gly Ile Arg Tyr Gly Thr Val Gly
                85                  90                  95

Gly Gly Leu Ala Arg Phe Gln Ala Ala Gln Pro Ile Gly Tyr Gln Gly
                100                 105                 110

Arg Val Asn Ala Thr Val Gln Ser Pro Asn Cys Ala Gln Phe Pro Glu
            115                 120                 125

Leu Asp Arg Leu Arg Leu Ser Glu Ser Arg Gly Glu Asn Val Asp Asp
            130                 135                 140

Cys Leu Thr Leu Asp Ile Tyr Ala Pro Glu Gly Ala Asn Gln Leu Pro
145                 150                 155                 160

Val Leu Val Phe Val His Gly Glu Met Leu Phe Asp Gly Gly Ser Glu
                165                 170                 175

Glu Ala Gln Pro Asp Tyr Val Leu Glu Lys Asp Val Leu Leu Val Ser
                180                 185                 190

Ile Asn Tyr Arg Leu Ala Pro Phe Gly Phe Leu Ser Ala Leu Thr Asp
            195                 200                 205

Glu Leu Pro Gly Asn Val Ala Leu Ser Asp Leu Gln Leu Ala Leu Glu
            210                 215                 220

Trp Leu Gln Arg Asn Val Val His Phe Gly Gly Asn Ala Gly Gln Val
225                 230                 235                 240

Thr Leu Val Gly Gln Ala Gly Gly Ala Thr Leu Ala His Ala Leu Ser
                245                 250                 255

Leu Ser Gly Arg Ala Gly Asn Leu Phe Gln Gln Leu Ile Leu Gln Ser
            260                 265                 270

Gly Thr Ala Leu Asn Pro Tyr Leu Ile Asp Asn Gln Pro Leu Asp Thr
            275                 280                 285

Leu Ser Thr Phe Ala Arg Leu Ala Arg Cys Pro Pro Ser Ile Asn
        290                 295                 300

Pro Ser Ala Gln Gly Leu Lys Pro Leu Tyr Asp Cys Leu Ala Arg Leu
305                 310                 315                 320

Pro Thr Ser Gln Leu Val Ala Ala Phe Glu Gln Leu Leu Gln Asn
            325                 330                 335

Glu His Leu Gly Leu Thr Gln Leu Gly Gly Phe Lys Leu Val Val Gly
            340                 345                 350

Asp Pro Leu Gly Phe Leu Pro Ser His Pro Ala Ser Leu Ala Thr Asn
            355                 360                 365
```

```
Ser Ser Leu Ala Leu Pro Met Ile Ile Gly Ala Thr Lys Asp Ala Ser
    370                 375                 380

Ala Phe Ile Val Ser Arg Ile Tyr Asp Gln Leu Ala Arg Leu Gln Ser
385                 390                 395                 400

Arg Asn Val Ser Asp Tyr Ile Asp Val Val Leu Arg His Thr Ala Pro
                405                 410                 415

Pro Ser Glu His Arg Leu Trp Lys Gln Trp Ala Leu Arg Glu Ile Phe
            420                 425                 430

Thr Pro Ile Gln Glu Gln Thr Ala Ser Leu Gln Thr Val Ala Pro Gly
        435                 440                 445

Leu Leu Glu Leu Ser Asn Tyr Ile Leu Tyr Arg Ala Pro Val Ile Asn
    450                 455                 460

Ser Ile Ser Gln Ser Tyr Arg Ser Val Pro Ala Tyr Leu Tyr Thr Phe
465                 470                 475                 480

Asp Tyr Arg Gly Glu His His Arg Phe Gly His Leu Ser Asn Pro Leu
                485                 490                 495

Pro Phe Gly Val Asp Ala Ser Leu Ser Asp Asp Ser Val Tyr Leu Phe
            500                 505                 510

Pro Tyr Pro Pro Glu Ala Ser Arg Leu Asn Pro Leu Asp Arg Ser Leu
        515                 520                 525

Ser Arg Ala Leu Val Thr Met Trp Val Asn Phe Ala Thr Thr Gly Val
    530                 535                 540

Pro Asn Pro Ser Ser Gly Val Trp Pro Gln Ala Thr Ser Glu Tyr Gly
545                 550                 555                 560

Pro Phe Leu Arg Phe Thr Asn Asn Gln Gln Ser Pro Leu Glu Leu Asp
                565                 570                 575

Pro His Phe Gly Glu Gly Ile Tyr Leu Pro Asn Tyr Arg Val Ile Tyr
            580                 585                 590

Lys Pro Thr Thr Asn Phe Ser Pro Pro Ile Thr Thr Thr Thr Thr Thr
        595                 600                 605

Thr Thr Thr Thr Thr Thr Thr Ser Arg Pro Tyr Ala Tyr Asn Pro Tyr
    610                 615                 620

Ala Asn Trp Gln Asn Arg Pro Ser Gln Gln His Pro Asn Trp His Pro
625                 630                 635                 640

Ala Asp Pro Glu Tyr Val Arg Ala Gln Glu Ala Arg Gln Gln Glu Phe
                645                 650                 655

Ile Arg Glu Arg Glu Gln Arg Arg Glu Gln Leu Arg Asp Gln
            660                 665                 670

Gln Arg Tyr Pro Gln Gln Glu Pro Arg Glu Gln Asp Glu Arg Ile
        675                 680                 685

Arg Gln Gln Arg Glu Gln Glu Glu Arg Leu Arg Gln Gln Arg Glu Gln
    690                 695                 700

Glu Glu Arg Leu Arg Gln Gln Arg Glu Leu Glu Glu Arg Ile Arg Gln
705                 710                 715                 720

Gln Gln Glu Arg Glu Gln Tyr Glu Arg Glu Gln Glu Arg Glu Gln
                725                 730                 735

Arg Glu Arg Glu Glu Leu Glu Arg Gln Arg Glu Arg Glu Gln Gln
            740                 745                 750

Gln Pro Glu Gln Gln Pro Glu Tyr Asn Pro Glu Pro Val Asn Pro Trp
        755                 760                 765

Gly Tyr Pro Val Gln Glu Pro Gln Pro Asp Asp Asn Pro Glu Asp Gly
    770                 775                 780

Arg Leu Pro Tyr Pro Ser Tyr Glu Gln Tyr Gly Pro Glu Gly Asn Glu
```

```
785                 790                 795                 800

Asn Leu Pro Glu Thr Asp Ala Asn Arg Asn Phe Ser Glu Glu Asp Arg
                805                 810                 815

Glu Gln Gln Gln Gln Glu Gln Leu Arg Arg Glu Gln Gln Glu Gln Gln
            820                 825                 830

Glu Arg Glu Tyr Gln Leu Gln Leu Glu Arg Glu Gln Gln Glu Arg Glu
        835                 840                 845

Gln Gln Glu Arg Gly Gln Gln Glu Pro Gly Pro Glu Glu Tyr Pro Ser
    850                 855                 860

Tyr Glu Glu Tyr Ser Arg Ala Leu Gln Glu Lys Asn Ala Glu Arg Asp
865                 870                 875                 880

Arg Ile Tyr Ala Glu Glu Gln Glu Arg Glu Arg Gln Gln Gln Glu Thr
                885                 890                 895

Leu Leu Gln Glu Asn Gln Gln His Pro Glu Gln Ser Leu Pro Glu Glu
            900                 905                 910

Gln Pro Thr His Pro Asn Tyr Asp Gly Asp Arg Ser Tyr Ala Glu Glu
        915                 920                 925

Gln Glu Arg Glu Gln Gln Arg Arg Asp Gln Val Glu Gln Glu Arg Glu
    930                 935                 940

Glu Gln Pro Asp Glu Asp Gln Gly Glu Glu Tyr Glu Arg Leu Pro Asp
945                 950                 955                 960
Glu Glu Glu Ala Ala Glu Gln Asp Val Leu Lys Val Glu Asp Phe Pro
                965                 970                 975

Ser Tyr Glu Ala Tyr Leu Glu Ala Ala Thr Lys Leu Arg Glu Glu Gln
            980                 985                 990

Glu Glu Gln Glu Lys Leu Glu Glu  Glu Arg Tyr Arg Ala  Gln Gln Glu
        995                 1000                 1005

Glu Glu  Asp Arg Ile Gln Ala  Glu Arg Glu Arg Asn  Ser Arg Asn
    1010                 1015                 1020

<210> SEQ ID NO 6
<211> LENGTH: 564
<212> TYPE: PRT
<213> ORGANISM: Heliothis virescens

<400> SEQUENCE: 6

Met Thr Ser His Val Leu Ala Leu Ala Phe Leu Leu His Ala Cys Thr
1               5                   10                  15

Ala Leu Ala Trp Gln Glu Thr Asn Ser Arg Ser Val Val Ala His Leu
            20                  25                  30

Asp Ser Gly Ile Ile Arg Gly Val Pro Arg Ser Ala Asp Gly Ile Lys
        35                  40                  45

Phe Ala Ser Phe Leu Gly Val Pro Tyr Ala Lys Gln Pro Val Gly Glu
    50                  55                  60

Leu Arg Phe Lys Glu Leu Glu Pro Leu Glu Pro Trp Asp Asn Ile Leu
65                  70                  75                  80

Asn Ala Thr Asn Glu Gly Pro Ile Cys Phe Gln Thr Asp Val Leu Tyr
                85                  90                  95

Gly Arg Leu Met Ala Ala Ser Glu Met Ser Glu Ala Cys Ile Tyr Ala
            100                 105                 110

Asn Ile His Val Pro Trp Gln Ser Leu Pro Arg Val Arg Gly Thr Thr
        115                 120                 125

Pro Leu Arg Pro Ile Leu Val Phe Ile His Gly Gly Gly Phe Ala Phe
    130                 135                 140

Gly Ser Gly His Glu Asp Leu His Gly Pro Glu Tyr Leu Val Thr Lys
```

```
            145                 150                 155                 160
        Asn Val Ile Val Ile Thr Phe Asn Tyr Arg Leu Asn Val Phe Gly Phe
                        165                 170                 175

Leu Ser Met Asn Thr Thr Lys Ile Pro Gly Asn Ala Gly Leu Arg Asp
                        180                 185                 190

Gln Val Thr Leu Leu Arg Trp Val Gln Arg Asn Ala Lys Asn Phe Gly
                        195                 200                 205

Gly Asp Pro Ser Asp Ile Thr Ile Ala Gly Gln Ser Ala Gly Ala Ser
                    210                 215                 220

Ala Ala His Leu Leu Thr Leu Ser Lys Ala Thr Glu Gly Leu Phe Lys
        225                 230                 235                 240

Arg Ala Ile Leu Met Ser Gly Thr Gly Met Ser Tyr Phe Phe Thr Thr
                            245                 250                 255

Ser Pro Leu Phe Ala Ala Tyr Ile Ser Lys Gln Leu Leu Gln Ile Leu
                        260                 265                 270

Gly Ile Asn Glu Thr Asp Pro Glu Glu Ile His Arg Gln Leu Ile Asp
                    275                 280                 285

Leu Pro Ala Glu Lys Leu Asn Glu Ala Asn Ala Val Leu Ile Glu Gln
                290                 295                 300

Ile Gly Leu Thr Thr Phe Leu Pro Ile Val Glu Ser Pro Leu Pro Gly
        305                 310                 315                 320

Val Thr Thr Ile Ile Asp Asp Pro Glu Ile Leu Ile Ala Glu Gly
                            325                 330                 335

Arg Gly Lys Asn Val Pro Leu Leu Ile Gly Phe Thr Ser Ser Glu Cys
                        340                 345                 350

Glu Thr Phe Arg Asn Arg Leu Leu Asn Phe Asp Leu Val Lys Lys Ile
                        355                 360                 365

Gln Asp Asn Pro Thr Ile Ile Ile Pro Pro Lys Leu Leu Phe Met Thr
                    370                 375                 380

Pro Pro Glu Leu Leu Met Glu Leu Ala Lys Thr Ile Glu Arg Lys Tyr
        385                 390                 395                 400

Tyr Asn Gly Thr Ile Ser Ile Asp Asn Phe Val Lys Ser Cys Ser Asp
                            405                 410                 415

Gly Phe Tyr Glu Tyr Pro Ala Leu Lys Leu Ala Gln Lys Arg Ala Glu
                        420                 425                 430

Thr Gly Gly Ala Pro Leu Tyr Leu Tyr Arg Phe Ala Tyr Glu Gly Gln
                    435                 440                 445

Asn Ser Ile Ile Lys Lys Val Met Gly Leu Asn His Glu Gly Val Gly
                450                 455                 460

His Ile Glu Asp Leu Thr Tyr Val Phe Lys Val Asn Ser Met Ser Glu
        465                 470                 475                 480

Ala Leu His Ala Ser Pro Ser Glu Asn Asp Val Lys Met Lys Asn Leu
                            485                 490                 495

Met Thr Gly Tyr Phe Leu Asn Phe Ile Lys Cys Ser Gln Pro Thr Cys
                        500                 505                 510

Glu Asp Asn Asn Ser Leu Glu Val Trp Pro Ala Asn Asn Gly Met Gln
                    515                 520                 525

Tyr Glu Asp Ile Val Ser Pro Thr Ile Ile Arg Ser Lys Glu Phe Ala
                530                 535                 540

Ser Arg Gln Gln Asp Ile Ile Glu Phe Phe Asp Ser Phe Thr Ser Arg
        545                 550                 555                 560

Ser Pro Leu Glu
```

<210> SEQ ID NO 7
<211> LENGTH: 540
<212> TYPE: PRT
<213> ORGANISM: Culex pipiens quinquefasciatus

<400> SEQUENCE: 7

Met Ser Leu Glu Ser Leu Thr Val Gln Thr Lys Tyr Gly Pro Val Arg
1               5                   10                  15

Gly Lys Arg Asn Val Ser Leu Leu Gly Gln Glu Tyr Val Ser Phe Gln
            20                  25                  30

Gly Ile Pro Tyr Ala Arg Ala Pro Glu Gly Glu Leu Arg Phe Lys Ala
        35                  40                  45

Pro Val Pro Pro Gln Lys Trp Thr Glu Thr Leu Asp Cys Thr Gln Gln
    50                  55                  60

Cys Glu Pro Cys Tyr His Phe Asp Arg Arg Leu Gln Lys Ile Val Gly
65                  70                  75                  80

Cys Glu Asp Ser Leu Lys Ile Asn Val Phe Ala Lys Glu Ile Asn Pro
                85                  90                  95

Ser Thr Pro Leu Pro Val Met Leu Tyr Ile Tyr Gly Gly Phe Thr
            100                 105                 110

Glu Gly Thr Ser Gly Thr Glu Leu Tyr Gly Pro Asp Phe Leu Val Gln
            115                 120                 125

Lys Asp Ile Val Leu Val Ser Phe Asn Tyr Arg Ile Gly Ala Leu Gly
130                 135                 140

Phe Leu Cys Cys Gln Ser Glu Gln Asp Gly Val Pro Gly Asn Ala Gly
145                 150                 155                 160

Leu Lys Asp Gln Asn Leu Ala Ile Arg Trp Val Leu Glu Asn Ile Ala
                165                 170                 175

Ala Phe Gly Gly Asp Pro Lys Arg Val Thr Leu Ala Gly His Ser Ala
            180                 185                 190

Gly Ala Ala Ser Val Gln Tyr His Leu Ile Ser Asp Ala Ser Lys Asp
        195                 200                 205

Leu Phe Gln Arg Arg Ile Val Met Ser Gly Ser Thr Tyr Ser Ser Trp
    210                 215                 220

Ser Leu Thr Arg Gln Arg Asn Trp Val Glu Lys Leu Ala Lys Ala Ile
225                 230                 235                 240

Gly Trp Asp Gly Gln Gly Gly Glu Ser Gly Ala Leu Arg Phe Leu Arg
                245                 250                 255

Arg Ala Lys Pro Glu Asp Ile Val Ala His Gln Glu Lys Leu Leu Thr
            260                 265                 270

Asp Gln Asp Met Gln Asp Asp Ile Phe Thr Pro Phe Gly Pro Thr Val
        275                 280                 285

Glu Pro Tyr Leu Thr Glu Gln Cys Ile Ile Pro Lys Ala Pro Phe Glu
    290                 295                 300

Met Ala Arg Thr Ala Trp Gly Asp Lys Ile Asp Ile Met Ile Gly Gly
305                 310                 315                 320

Thr Ser Glu Glu Gly Leu Leu Leu Gln Lys Ile Lys Leu His Pro
                325                 330                 335

Glu Leu Leu Ser His Pro His Leu Phe Leu Gly Asn Val Pro Pro Asn
            340                 345                 350

Leu Lys Ile Ser Met Glu Lys Arg Ile Glu Phe Ala Ala Lys Leu Lys
        355                 360                 365

Gln Arg Tyr Tyr Pro Asp Ser Ile Pro Ser Met Glu Asn Asn Leu Gly
    370                 375                 380

Tyr Val His Met Met Ser Asp Arg Val Phe Trp His Gly Leu His Arg

```
                385                 390                 395                 400
Thr Ile Leu Ala Arg Ala Ala Arg Ser Arg Ala Arg Thr Phe Val Tyr
                    405                 410                 415

Arg Ile Cys Leu Asp Ser Glu Phe Tyr Asn His Tyr Arg Ile Met Met
                420                 425                 430

Ile Asp Pro Lys Leu Arg Gly Thr Ala His Ala Asp Glu Leu Ser Tyr
                435                 440                 445

Leu Phe Ser Asn Phe Thr Gln Gln Val Pro Gly Lys Glu Thr Phe Glu
            450                 455                 460

Tyr Arg Gly Leu Gln Thr Leu Val Asp Val Phe Ser Ala Phe Val Ile
465                 470                 475                 480

Asn Gly Asp Pro Asn Cys Gly Met Thr Ala Lys Gly Val Val Phe
                485                 490                 495

Glu Pro Asn Ala Gln Thr Lys Pro Thr Phe Lys Cys Leu Asn Ile Ala
                500                 505                 510

Asn Asp Gly Val Ala Phe Val Asp Tyr Pro Asp Ala Asp Arg Leu Asp
            515                 520                 525

Met Trp Asp Ala Met Tyr Val Asn Asp Glu Leu Phe
            530                 535                 540

<210> SEQ ID NO 8
<211> LENGTH: 544
<212> TYPE: PRT
<213> ORGANISM: Drosophila melanogaster

<400> SEQUENCE: 8

Met Asn Tyr Val Gly Leu Gly Leu Ile Thr Val Leu Ser Cys Leu Trp
1               5                   10                  15

Leu Gly Ser Asn Ala Ser Asp Ile Asp Asp Pro Leu Leu Val Gln Leu
                20                  25                  30

Pro Gln Gly Lys Leu Arg Gly Arg Asp Asn Gly Ser Tyr Tyr Ser Tyr
            35                  40                  45

Glu Ser Ile Pro Tyr Ala Glu Pro Pro Ile Gly Asp Leu Arg Phe Glu
    50                  55                  60

Ala Pro Glu Pro Tyr Lys Gln Lys Trp Ser Asp Ile Phe Asp Ala Thr
65                  70                  75                  80

Lys Thr Pro Val Ala Cys Leu Gln Trp Asp Gln Phe Thr Pro Gly Ala
                85                  90                  95

Asn Lys Leu Val Gly Glu Glu Asp Cys Leu Thr Val Ser Val Tyr Lys
            100                 105                 110

Pro Lys Asn Ser Lys Arg Asn Ser Phe Pro Val Val Ala His Ile His
        115                 120                 125

Gly Gly Ala Phe Met Phe Gly Ala Ala Trp Gln Asn Gly His Glu Asn
    130                 135                 140

Val Met Arg Glu Gly Lys Phe Ile Leu Val Lys Ile Ser Tyr Arg Leu
145                 150                 155                 160

Gly Pro Leu Gly Phe Val Ser Thr Gly Asp Arg Asp Leu Pro Gly Asn
                165                 170                 175

Tyr Gly Leu Lys Asp Gln Arg Leu Ala Leu Lys Trp Ile Lys Gln Asn
            180                 185                 190

Ile Ala Ser Phe Gly Gly Glu Pro Gln Asn Val Leu Leu Val Gly His
        195                 200                 205

Ser Ala Gly Gly Ala Ser Val His Leu Gln Met Leu Arg Glu Asp Phe
    210                 215                 220

Gly Gln Leu Ala Arg Ala Ala Phe Ser Phe Ser Gly Asn Ala Leu Asp
```

```
                    225                 230                 235                 240

Pro Trp Val Ile Gln Lys Gly Ala Arg Gly Ala Phe Glu Leu Gly
                245                 250                 255

Arg Asp Val Gly Cys Glu Ser Ala Glu Asp Ser Ala Ser Leu Lys Lys
                260                 265                 270

Cys Leu Lys Ser Lys Pro Ala Ser Glu Leu Val Thr Ala Val Arg Lys
                275                 280                 285

Phe Leu Ile Phe Ser Tyr Val Pro Phe Ala Pro Phe Ser Pro Val Leu
                290                 295                 300

Glu Pro Ser Asp Ala Pro Asp Ala Ile Ile Thr Gln Asp Pro Arg Asp
305                 310                 315                 320

Val Ile Lys Ser Gly Lys Phe Gly Gln Val Pro Trp Ala Val Ser Tyr
                325                 330                 335

Val Thr Glu Asp Gly Gly Tyr Asn Ala Ala Leu Leu Leu Lys Glu Arg
                340                 345                 350

Lys Ser Gly Ile Val Ile Asp Asp Leu Asn Glu Arg Trp Leu Glu Leu
                355                 360                 365

Ala Pro Tyr Leu Leu Phe Tyr Arg Asp Thr Lys Thr Lys Lys Asp Met
                370                 375                 380

Asp Asp Tyr Ser Arg Lys Ile Lys Gln Glu Tyr Ile Gly Asn Gln Arg
385                 390                 395                 400

Phe Asp Ile Glu Ser Tyr Ser Glu Val Gln Arg Leu Phe Thr Asp Ile
                405                 410                 415

Leu Phe Lys Asn Ser Thr Gln Glu Ser Leu Asp Leu His Arg Lys Tyr
                420                 425                 430

Gly Lys Ser Pro Ala Tyr Ala Tyr Val Tyr Asp Asn Pro Ala Glu Lys
                435                 440                 445

Gly Ile Ala Gln Val Leu Ala Asn Arg Thr Asp Tyr Asp Phe Gly Thr
                450                 455                 460

Val His Gly Asp Asp Tyr Phe Leu Ile Phe Glu Asn Phe Val Arg Asp
465                 470                 475                 480

Val Glu Met Arg Pro Asp Glu Gln Ile Ile Ser Arg Asn Phe Ile Asn
                485                 490                 495

Met Leu Ala Asp Phe Ala Ser Ser Asp Asn Gly Ala Leu Lys Tyr Gly
                500                 505                 510

Glu Cys Asp Phe Lys Asp Asn Val Gly Ser Glu Lys Phe Gln Leu Leu
                515                 520                 525

Ala Ile Tyr Ile Asp Gly Cys Gln Asn Arg Gln His Val Glu Phe Pro
                530                 535                 540

<210> SEQ ID NO 9
<211> LENGTH: 544
<212> TYPE: PRT
<213> ORGANISM: Drosophila melanogaster

<400> SEQUENCE: 9

Met Ser Ile Phe Lys Arg Leu Leu Cys Leu Thr Leu Leu Trp Ile Ala
1               5                   10                  15

Ala Leu Glu Ser Glu Ala Asp Pro Leu Ile Val Glu Ile Thr Asn Gly
                20                  25                  30

Lys Ile Arg Gly Lys Asp Asn Gly Leu Tyr Tyr Ser Tyr Glu Ser Ile
                35                  40                  45

Pro Tyr Ala Glu His Pro Thr Gly Ala Leu Arg Phe Glu Ala Pro Gln
                50                  55                  60

Pro Tyr Ser His His Trp Thr Asp Val Phe Asn Ala Thr Gln Ser Pro
```

```
            65                  70                  75                  80
Val Glu Cys Met Gln Trp Asn Gln Phe Ile Asn Glu Asn Asn Lys Leu
                    85                  90                  95

Met Gly Asp Glu Asp Cys Leu Thr Val Ser Ile Tyr Lys Pro Lys Lys
                100                 105                 110

Pro Asn Arg Ser Ser Phe Pro Val Val Leu Leu His Gly Gly Ala
            115                 120                 125

Phe Met Phe Gly Ser Gly Ser Ile Tyr Gly His Asp Ser Ile Met Arg
        130                 135                 140

Glu Gly Thr Leu Leu Val Val Lys Ile Ser Tyr Arg Leu Gly Pro Leu
145                 150                 155                 160

Gly Phe Ala Ser Thr Gly Asp Arg His Leu Pro Gly Asn Tyr Gly Leu
                165                 170                 175

Lys Asp Gln Arg Leu Ala Leu Gln Trp Ile Lys Lys Asn Ile Ala His
            180                 185                 190

Phe Gly Gly Met Pro Asp Asn Ile Val Leu Ile Gly His Ser Ala Gly
        195                 200                 205

Gly Ala Ser Ala His Leu Gln Leu Leu His Glu Asp Phe Lys His Leu
    210                 215                 220

Ala Lys Gly Ala Ile Ser Val Ser Gly Asn Ala Leu Asp Pro Trp Val
225                 230                 235                 240

Ile Gln Gln Gly Gly Arg Arg Ala Phe Glu Leu Gly Arg Ile Val
                245                 250                 255

Gly Cys Gly His Thr Asn Val Ser Ala Glu Leu Lys Asp Cys Leu Lys
                260                 265                 270

Ser Lys Pro Ala Ser Asp Ile Val Ser Ala Val Arg Ser Phe Leu Val
            275                 280                 285

Phe Ser Tyr Val Pro Phe Ser Ala Phe Gly Pro Val Val Glu Pro Ser
        290                 295                 300

Asp Ala Pro Asp Ala Phe Leu Thr Glu Asp Pro Arg Ala Val Ile Lys
305                 310                 315                 320

Ser Gly Lys Phe Ala Gln Val Pro Trp Ala Val Thr Tyr Thr Thr Glu
                325                 330                 335

Asp Gly Gly Tyr Asn Ala Ala Gln Leu Leu Glu Arg Asn Lys Leu Thr
            340                 345                 350

Gly Glu Ser Trp Ile Asp Leu Leu Asn Asp Arg Trp Phe Asp Trp Ala
        355                 360                 365

Pro Tyr Leu Leu Phe Tyr Arg Asp Ala Lys Lys Thr Ile Lys Asp Met
    370                 375                 380

Asp Asp Leu Ser Phe Asp Leu Arg Gln Gln Tyr Leu Ala Asp Arg Arg
385                 390                 395                 400

Phe Ser Val Glu Ser Tyr Trp Asn Val Gln Arg Met Phe Thr Asp Val
                405                 410                 415

Leu Phe Lys Asn Ser Val Pro Ser Ala Ile Asp Leu His Arg Lys Tyr
            420                 425                 430

Gly Lys Ser Pro Val Tyr Ser Phe Val Tyr Asp Asn Pro Thr Asp Ser
        435                 440                 445

Gly Val Gly Gln Leu Leu Ser Asn Arg Thr Asp Val His Phe Gly Thr
    450                 455                 460

Val His Gly Asp Asp Phe Phe Leu Ile Phe Asn Thr Ala Ala Tyr Arg
465                 470                 475                 480

Ile Gly Ile Arg Pro Asp Glu Glu Val Ile Ser Lys Lys Phe Ile Gly
                485                 490                 495
```

Met Leu Glu Asp Phe Ala Leu Asn Asp Lys Gly Thr Leu Thr Phe Gly
            500                 505                 510

Glu Cys Asn Phe Gln Asn Asn Val Asn Ser Lys Glu Tyr Gln Val Leu
            515                 520                 525

Arg Ile Ser Arg Asn Ala Cys Lys Asn Glu Glu Tyr Ala Arg Phe Pro
            530                 535                 540

<210> SEQ ID NO 10
<211> LENGTH: 746
<212> TYPE: PRT
<213> ORGANISM: Drosophila melanogaster

<400> SEQUENCE: 10

Met His Met Ala Met Gln Ala Ala Leu His Phe Ile Tyr Ser Leu Glu
1               5                   10                  15

Asn Trp Gln Ile Arg Glu Ser Glu Ser Phe Lys His Gln Thr Met Met
            20                  25                  30

Cys Ser Ala Thr His Gly Arg His Val Gln Val Ala Ile Val Ala Ala
        35                  40                  45

Glu Ala Asn Ser Thr Gly Met Arg Leu Val Ala Pro Gly Arg His Pro
    50                  55                  60

Glu Ser Ala Arg His Thr Thr Ser Val Pro Ser Tyr Pro Ala Ser Arg
65                  70                  75                  80

Asn Arg Glu Ser Ala Thr Ala Arg Glu Pro Thr Ser Gly Gln Cys
            85                  90                  95

Gln Met Ala Ile Ser Cys Arg Gln Ser Arg Val Leu Pro Met Ser Leu
            100                 105                 110

Pro Leu Pro Leu Thr Ile Pro Leu Pro Leu Val Leu Val Leu Ser Leu
            115                 120                 125

His Leu Ser Gly Val Cys Gly Val Ile Asp Arg Leu Val Val Gln Thr
    130                 135                 140

Ser Ser Gly Pro Val Arg Gly Arg Ser Val Thr Val Gln Gly Arg Glu
145                 150                 155                 160

Val His Val Tyr Thr Gly Ile Pro Tyr Ala Lys Pro Pro Val Glu Asp
            165                 170                 175

Leu Arg Phe Arg Lys Pro Val Pro Ala Glu Pro Trp His Gly Val Leu
            180                 185                 190

Asp Ala Thr Gly Leu Ser Ala Thr Cys Val Gln Glu Arg Tyr Glu Tyr
            195                 200                 205

Phe Pro Gly Phe Ser Gly Glu Glu Ile Trp Asn Pro Asn Thr Asn Val
    210                 215                 220

Ser Glu Asp Cys Leu Tyr Ile Asn Val Trp Ala Pro Ala Lys Ala Arg
225                 230                 235                 240

Leu Arg His Gly Arg Gly Ala Asn Gly Gly Glu His Pro Asn Gly Lys
            245                 250                 255

Gln Ala Asp Thr Asp His Leu Ile His Asn Gly Asn Pro Gln Asn Thr
            260                 265                 270

Thr Asn Gly Leu Pro Ile Leu Ile Trp Ile Tyr Gly Gly Gly Phe Met
        275                 280                 285

Thr Gly Ser Ala Thr Leu Asp Ile Tyr Asn Ala Asp Ile Met Ala Ala
    290                 295                 300

Val Gly Asn Val Ile Val Ala Ser Phe Gln Tyr Arg Val Gly Ala Phe
305                 310                 315                 320

Gly Phe Leu His Leu Ala Pro Glu Met Pro Ser Glu Phe Ala Glu Glu
            325                 330                 335

```
Ala Pro Gly Asn Val Gly Leu Trp Asp Gln Ala Leu Ala Ile Arg Trp
            340                 345                 350

Leu Lys Asp Asn Ala His Ala Phe Gly Asn Pro Glu Trp Met Thr
        355                 360                 365

Leu Phe Gly Glu Ser Ala Gly Ser Ser Val Asn Ala Gln Leu Met
370                 375                 380

Ser Pro Val Thr Arg Gly Leu Val Lys Arg Gly Met Met Gln Ser Gly
385                 390                 395                 400

Thr Met Asn Ala Pro Trp Ser His Met Thr Ser Glu Lys Ala Val Glu
                405                 410                 415

Ile Gly Lys Ala Leu Ile Asn Asp Cys Asn Cys Asn Ala Ser Met Leu
                420                 425                 430

Lys Thr Asn Pro Ala His Val Met Ser Cys Met Arg Ser Val Asp Ala
        435                 440                 445

Lys Thr Ile Ser Val Gln Gln Trp Asn Ser Tyr Ser Gly Ile Leu Ser
450                 455                 460

Phe Pro Ser Ala Pro Thr Ile Asp Gly Ala Phe Leu Pro Ala Asp Pro
465                 470                 475                 480

Met Thr Leu Met Lys Thr Ala Asp Leu Lys Asp Tyr Asp Ile Leu Met
                485                 490                 495

Gly Asn Val Arg Asp Glu Gly Thr Tyr Phe Leu Leu Tyr Asp Phe Ile
                500                 505                 510

Asp Tyr Phe Asp Lys Asp Asp Ala Thr Ala Leu Pro Arg Asp Lys Tyr
        515                 520                 525

Leu Glu Ile Met Asn Asn Ile Phe Gly Lys Ala Thr Gln Ala Glu Arg
530                 535                 540

Glu Ala Ile Ile Phe Gln Tyr Thr Ser Trp Glu Gly Asn Pro Gly Tyr
545                 550                 555                 560

Gln Asn Gln Gln Gln Ile Gly Arg Ala Val Gly Asp His Phe Phe Thr
                565                 570                 575

Cys Pro Thr Asn Glu Tyr Ala Gln Ala Leu Ala Glu Arg Gly Ala Ser
                580                 585                 590

Val His Tyr Tyr Tyr Phe Thr His Arg Thr Ser Thr Ser Leu Trp Gly
        595                 600                 605

Glu Trp Met Gly Val Leu His Gly Asp Glu Ile Glu Tyr Phe Phe Gly
610                 615                 620

Gln Pro Leu Asn Asn Ser Leu Gln Tyr Arg Pro Val Glu Arg Glu Leu
625                 630                 635                 640

Gly Lys Arg Met Leu Ser Ala Val Ile Glu Phe Ala Lys Thr Gly Asn
                645                 650                 655

Pro Ala Gln Asp Gly Glu Glu Trp Pro Asn Phe Ser Lys Glu Asp Pro
                660                 665                 670

Val Tyr Tyr Ile Phe Ser Thr Asp Asp Lys Ile Glu Lys Leu Ala Arg
        675                 680                 685

Gly Pro Leu Ala Ala Arg Cys Ser Phe Trp Asn Asp Tyr Leu Pro Lys
690                 695                 700

Val Arg Ser Trp Ala Gly Thr Cys Asp Gly Asp Ser Gly Ser Ala Ser
705                 710                 715                 720

Ile Ser Pro Arg Leu Gln Leu Leu Gly Ile Ala Ala Leu Ile Tyr Ile
                725                 730                 735

Cys Ala Ala Leu Arg Thr Lys Arg Val Phe
                740                 745

<210> SEQ ID NO 11
```

<211> LENGTH: 586
<212> TYPE: PRT
<213> ORGANISM: Torpedo californica

<400> SEQUENCE: 11

```
Met Asn Leu Leu Val Thr Ser Ser Leu Gly Val Leu Leu His Leu Val
1               5                   10                  15

Val Leu Cys Gln Ala Asp Asp His Ser Glu Leu Leu Val Asn Thr Lys
            20                  25                  30

Ser Gly Lys Val Met Gly Thr Arg Val Pro Val Leu Ser Ser His Ile
        35                  40                  45

Ser Ala Phe Leu Gly Ile Pro Phe Ala Glu Pro Val Gly Asn Met
    50                  55                  60

Arg Phe Arg Arg Pro Glu Pro Lys Lys Pro Trp Ser Gly Val Trp Asn
65                  70                  75                  80

Ala Ser Thr Tyr Pro Asn Asn Cys Gln Gln Tyr Val Asp Glu Gln Phe
                85                  90                  95

Pro Gly Phe Ser Gly Ser Glu Met Trp Asn Pro Asn Arg Glu Met Ser
            100                 105                 110

Glu Asp Cys Leu Tyr Leu Asn Ile Trp Val Pro Ser Pro Arg Pro Lys
        115                 120                 125

Ser Thr Thr Val Met Val Trp Ile Tyr Gly Gly Phe Tyr Ser Gly
    130                 135                 140

Ser Ser Thr Leu Asp Val Tyr Asn Gly Lys Tyr Leu Ala Tyr Thr Glu
145                 150                 155                 160

Glu Val Val Leu Val Ser Leu Ser Tyr Arg Val Gly Ala Phe Gly Phe
                165                 170                 175

Leu Ala Leu His Gly Ser Gln Glu Ala Pro Gly Asn Val Gly Leu Leu
            180                 185                 190

Asp Gln Arg Met Ala Leu Gln Trp Val His Asp Asn Ile Gln Phe Phe
        195                 200                 205

Gly Gly Asp Pro Lys Thr Val Thr Ile Phe Gly Glu Ser Ala Gly Gly
    210                 215                 220

Ala Ser Val Gly Met His Ile Leu Ser Pro Gly Ser Arg Asp Leu Phe
225                 230                 235                 240

Arg Arg Ala Ile Leu Gln Ser Gly Ser Pro Asn Cys Pro Trp Ala Ser
                245                 250                 255

Val Ser Val Ala Glu Gly Arg Arg Ala Val Glu Leu Gly Arg Asn
            260                 265                 270

Leu Asn Cys Asn Leu Asn Ser Asp Glu Glu Leu Ile His Cys Leu Arg
        275                 280                 285

Glu Lys Lys Pro Gln Glu Leu Ile Asp Val Glu Trp Asn Val Leu Pro
    290                 295                 300

Phe Asp Ser Ile Phe Arg Phe Ser Phe Val Pro Val Ile Asp Gly Glu
305                 310                 315                 320

Phe Phe Pro Thr Ser Leu Glu Ser Met Leu Asn Ser Gly Asn Phe Lys
                325                 330                 335

Lys Thr Gln Ile Leu Leu Gly Val Asn Lys Asp Glu Gly Ser Phe Phe
            340                 345                 350

Leu Leu Tyr Gly Ala Pro Gly Phe Ser Lys Asp Ser Glu Ser Lys Ile
        355                 360                 365

Ser Arg Glu Asp Phe Met Ser Gly Val Lys Leu Ser Val Pro His Ala
    370                 375                 380

Asn Asp Leu Gly Leu Asp Ala Val Thr Leu Gln Tyr Thr Asp Trp Met
385                 390                 395                 400
```

```
Asp Asp Asn Asn Gly Ile Lys Asn Arg Asp Gly Leu Asp Asp Ile Val
            405                 410                 415

Gly Asp His Asn Val Ile Cys Pro Leu Met His Phe Val Asn Lys Tyr
            420                 425                 430

Thr Lys Phe Gly Asn Gly Thr Tyr Leu Tyr Phe Phe Asn His Arg Ala
            435                 440                 445

Ser Asn Leu Val Trp Pro Glu Trp Met Gly Val Ile His Gly Tyr Glu
            450                 455                 460

Ile Glu Phe Val Phe Gly Leu Pro Leu Val Lys Glu Leu Asn Tyr Thr
465                 470                 475                 480

Ala Glu Glu Glu Ala Leu Ser Arg Arg Ile Met His Tyr Trp Ala Thr
                    485                 490                 495

Phe Ala Lys Thr Gly Asn Pro Asn Glu Pro His Ser Gln Glu Ser Lys
                500                 505                 510

Trp Pro Leu Phe Thr Thr Lys Glu Gln Lys Phe Ile Asp Leu Asn Thr
            515                 520                 525

Glu Pro Met Lys Val His Gln Arg Leu Arg Val Gln Met Cys Val Phe
            530                 535                 540

Trp Asn Gln Phe Leu Pro Lys Leu Leu Asn Ala Thr Ala Cys Asp Gly
545                 550                 555                 560

Glu Leu Ser Ser Ser Gly Thr Ser Ser Lys Gly Ile Ile Phe Tyr
                    565                 570                 575

Val Leu Phe Ser Ile Leu Tyr Leu Ile Phe
                580                 585

<210> SEQ ID NO 12
<211> LENGTH: 57
<212> TYPE: PRT
<213> ORGANISM: Homo sapiens

<400> SEQUENCE: 12

Arg Phe Leu Pro Lys Leu Leu Ser Ala Thr Ala Pro Pro Ser Leu Gly
1               5                   10                  15

Gly Ser Gln His Leu Pro Arg Leu His Pro Trp Gly Gly Cys Ser Glu
            20                  25                  30

Ala Arg Pro Pro Pro Ala Pro Pro Pro Pro Pro Ala Ser Pro Pro
            35                  40                  45

Leu Pro Leu Pro Pro Ala Ala Val
    50                  55

<210> SEQ ID NO 13
<211> LENGTH: 602
<212> TYPE: PRT
<213> ORGANISM: Homo sapiens

<400> SEQUENCE: 13

Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
            35                  40                  45

Phe Gly Gly Thr Val Thr Ala Phe Leu Gly Ile Pro Tyr Ala Gln Pro
        50                  55                  60

Pro Leu Gly Arg Leu Arg Phe Lys Lys Pro Gln Ser Leu Thr Lys Trp
65                  70                  75                  80
```

-continued

```
Ser Asp Ile Trp Asn Ala Thr Lys Tyr Ala Asn Ser Cys Cys Gln Asn
                 85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
        130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
        210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Thr Glu Ile
            275                 280                 285

Ile Lys Cys Leu Arg Asn Lys Asp Pro Gln Glu Ile Leu Leu Asn Glu
        290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
        370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510
```

```
Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
        530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
            595                 600

<210> SEQ ID NO 14
<211> LENGTH: 565
<212> TYPE: PRT
<213> ORGANISM: Rattus norvegicus

<400> SEQUENCE: 14

Met Arg Leu Tyr Pro Leu Val Trp Leu Phe Leu Ala Ala Cys Thr Ala
1               5                   10                  15

Trp Gly Tyr Pro Ser Ser Pro Val Val Asn Thr Val Lys Gly Lys
            20                  25                  30

Val Leu Gly Lys Tyr Val Asn Leu Glu Gly Phe Ala Gln Pro Val Ala
        35                  40                  45

Val Phe Leu Gly Ile Pro Phe Ala Lys Pro Pro Leu Gly Ser Leu Arg
50                  55                  60

Phe Ala Pro Pro Gln Pro Ala Glu Pro Trp Asn Phe Val Lys Asn Thr
65                  70                  75                  80

Thr Ser Tyr Pro Pro Met Cys Ser Gln Asp Ala Val Gly Gly Gln Val
            85                  90                  95

Leu Ser Glu Leu Phe Thr Asn Arg Lys Glu Asn Ile Pro Leu Gln Phe
        100                 105                 110

Ser Glu Asp Cys Leu Tyr Leu Asn Val Tyr Thr Pro Ala Asp Leu Thr
    115                 120                 125

Lys Asn Ser Arg Leu Pro Val Met Val Trp Ile His Gly Gly Gly Leu
        130                 135                 140

Val Val Gly Gly Ala Ser Thr Tyr Asp Gly Gln Val Leu Ser Ala His
145                 150                 155                 160

Glu Asn Val Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu His Trp Val Gln Asp Asn Ile Ala Asn Phe
        195                 200                 205

Gly Gly Asn Pro Gly Ser Val Thr Ile Phe Gly Glu Ser Ala Gly Gly
    210                 215                 220

Phe Ser Val Ser Ala Leu Val Leu Ser Pro Leu Ala Lys Asn Leu Phe
225                 230                 235                 240

His Arg Ala Ile Ser Glu Ser Gly Val Val Leu Thr Ser Ala Leu Ile
                245                 250                 255
```

```
Thr Thr Asp Ser Lys Pro Ile Ala Lys Leu Ile Ala Thr Leu Ser Gly
            260             265             270

Cys Lys Thr Thr Thr Ser Ala Val Met Val His Cys Leu Arg Gln Lys
        275             280             285

Thr Glu Asp Glu Leu Leu Glu Thr Ser Leu Lys Leu Asn Leu Phe Lys
    290             295             300

Leu Asp Leu Leu Gly Asn Pro Lys Glu Ser Tyr Pro Phe Leu Pro Thr
305             310             315             320

Val Ile Asp Gly Val Val Leu Pro Lys Thr Pro Glu Glu Ile Leu Ala
            325             330             335

Glu Lys Ser Phe Asn Thr Val Pro Tyr Ile Val Gly Ile Asn Lys Gln
            340             345             350

Glu Phe Gly Trp Ile Ile Pro Thr Leu Met Gly Tyr Pro Leu Ser Glu
            355             360             365

Gly Lys Leu Asp Gln Lys Thr Ala Lys Ser Leu Leu Trp Lys Ser Tyr
        370             375             380

Pro Thr Leu Lys Ile Ser Glu Lys Met Ile Pro Val Val Ala Glu Lys
385             390             395             400

Tyr Phe Gly Gly Thr Asp Asp Pro Ala Lys Arg Lys Asp Leu Phe Gln
            405             410             415

Asp Leu Val Ala Asp Val Ile Phe Gly Val Pro Ser Val Met Val Ser
            420             425             430

Arg Ser His Arg Asp Ala Gly Ala Pro Thr Phe Met Tyr Glu Phe Glu
            435             440             445

Tyr Arg Pro Ser Phe Val Ser Ala Met Arg Pro Lys Thr Val Ile Gly
    450             455             460

Asp His Gly Asp Glu Leu Phe Ser Val Phe Gly Ser Pro Phe Leu Lys
465             470             475             480

Asp Gly Ala Ser Glu Glu Glu Thr Asn Leu Ser Lys Met Val Met Lys
            485             490             495

Tyr Trp Ala Asn Phe Ala Arg Asn Gly Ser Pro Asn Gly Gly Gly Leu
            500             505             510

Pro His Trp Pro Glu Tyr Asp Gln Lys Glu Gly Tyr Leu Lys Ile Gly
    515             520             525

Ala Ser Thr Gln Ala Ala Gln Arg Leu Lys Asp Lys Glu Val Ala Phe
    530             535             540

Trp Ser Glu Leu Arg Ala Lys Glu Ala Ala Glu Glu Pro Ser His Trp
545             550             555             560

Lys His Val Glu Leu
            565
```